(12) United States Patent
Sanders et al.

(10) Patent No.: US 9,370,429 B1
(45) Date of Patent: *Jun. 21, 2016

(54) SYSTEM AND METHOD FOR MODIFYING TALOCALCANEAL RELATIONSHIP IN A FOOT

(71) Applicant: Foot Innovations, LLC, Tampa, FL (US)

(72) Inventors: Roy Sanders, Tampa, FL (US); Sergio Gutierrez, Tampa, FL (US)

(73) Assignee: Foot Innovations, LLC, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/042,485

(22) Filed: Sep. 30, 2013

Related U.S. Application Data

(63) Continuation of application No. 13/837,949, filed on Mar. 15, 2013, now Pat. No. 8,574,305.

(51) Int. Cl.
*A61F 2/42* (2006.01)

(52) U.S. Cl.
CPC ................. *A61F 2/42* (2013.01); *A61F 2/4202* (2013.01); *A61F 2/4225* (2013.01); *A61F 2002/4207* (2013.01); *A61F 2002/4217* (2013.01)

(58) Field of Classification Search
CPC .............. A61F 2/42; A61F 2002/4212; A61F 2002/4215; A61F 2002/4217; A61F 2002/422; A61F 2002/4223; A61F 2/2407; A61F 2/4225

USPC ........................................................ 623/21.18
See application file for complete search history.

(56) References Cited

U.S. PATENT DOCUMENTS

| | | | |
|---|---|---|---|
| 4,450,591 A | 5/1984 | Rappaport | |
| D274,359 S | 6/1984 | Christensen et al. | |
| 6,136,032 A | 10/2000 | Perice et al. | |
| 6,168,631 B1 | 1/2001 | Maxwell et al. | |
| D504,514 S | 4/2005 | Spalding | |
| 7,033,398 B2 | 4/2006 | Graham | |
| 2005/0177165 A1 | 8/2005 | Zang | |
| 2005/0177243 A1 | 8/2005 | Lepow et al. | |
| 2005/0197711 A1 | 9/2005 | Cachia | |
| 2005/0229433 A1 | 10/2005 | Cachia | |
| 2006/0004378 A1 | 1/2006 | Raines, Jr. et al. | |
| 2006/0190088 A1 | 8/2006 | Parks et al. | |
| 2007/0173954 A1 | 7/2007 | Lavi | |

OTHER PUBLICATIONS

Marketing Brochure: Nexa Orthopedics—Futura Coninical Subtalar Implant.
Marketing Brochure: The Biopro Implants—"The BioPro Horizon Subtalar".

*Primary Examiner* — David Isabella
*Assistant Examiner* — Suba Ganesan
(74) *Attorney, Agent, or Firm* — Foley & Lardner LLP; Christopher J. McKenna; Shabbi S. Khan

(57) ABSTRACT

A system for modifying a talocalcaneal spatial relationship in a foot in a body, including a subtalar spacer having an articulating surface and implanted in the sinus tarsi of the foot and a fastener that fastens the subtalar spacer to a bone surface in the foot, in which the articulating surface of the subtalar spacer directs relative movement between the calcaneus and the talus of the foot.

18 Claims, 23 Drawing Sheets

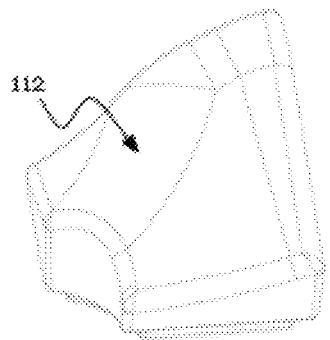
FIGURE 1A
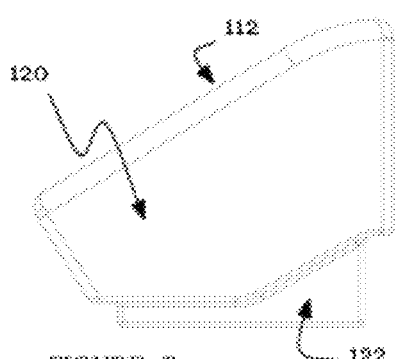
FIGURE 1B
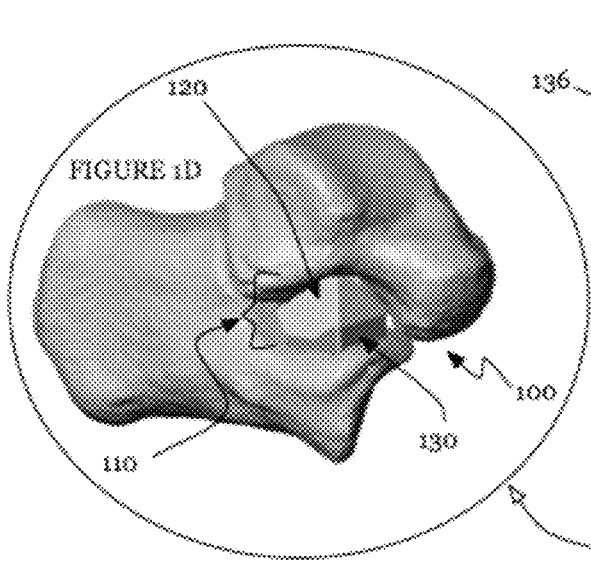
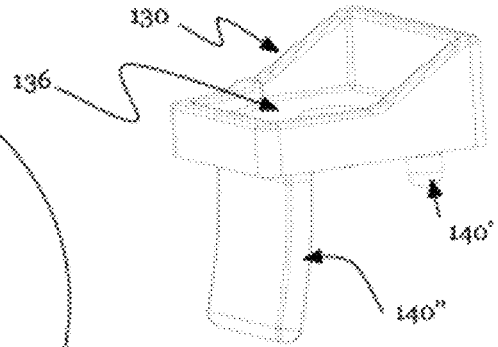
FIGURE 1C
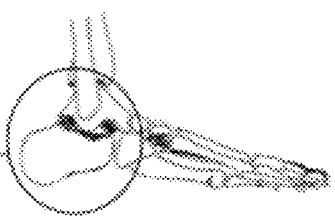

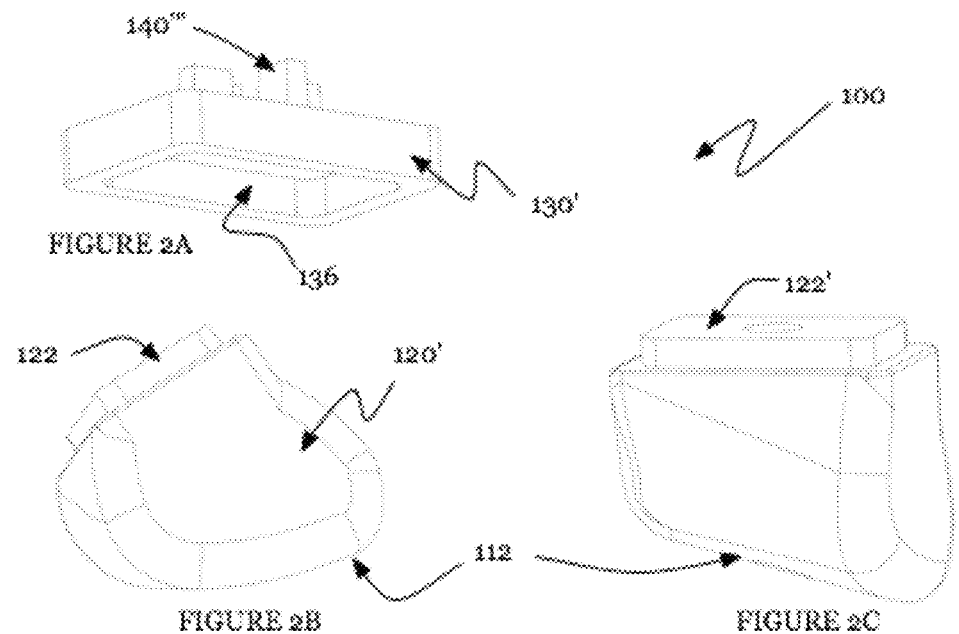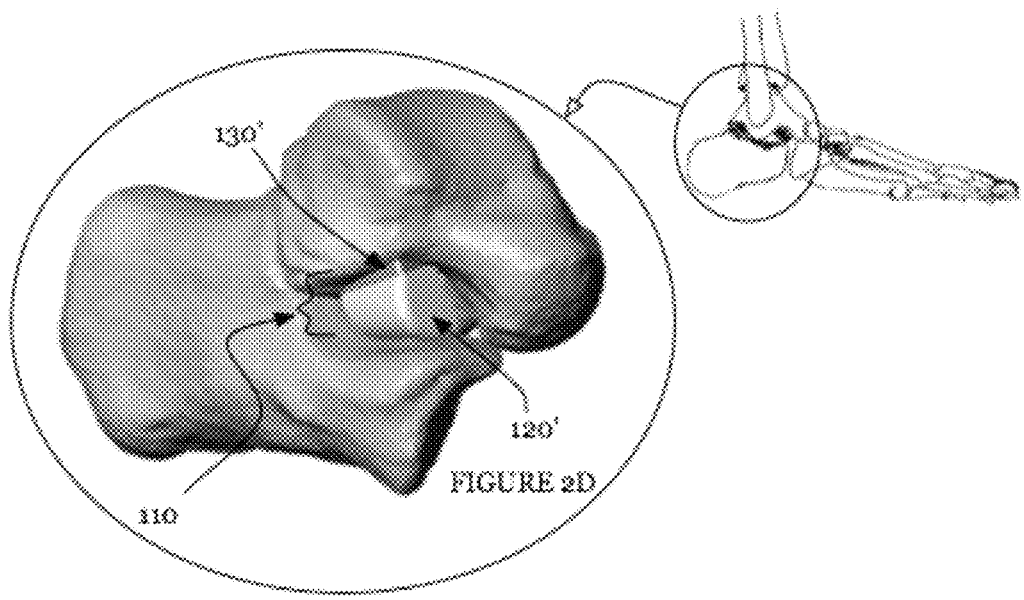

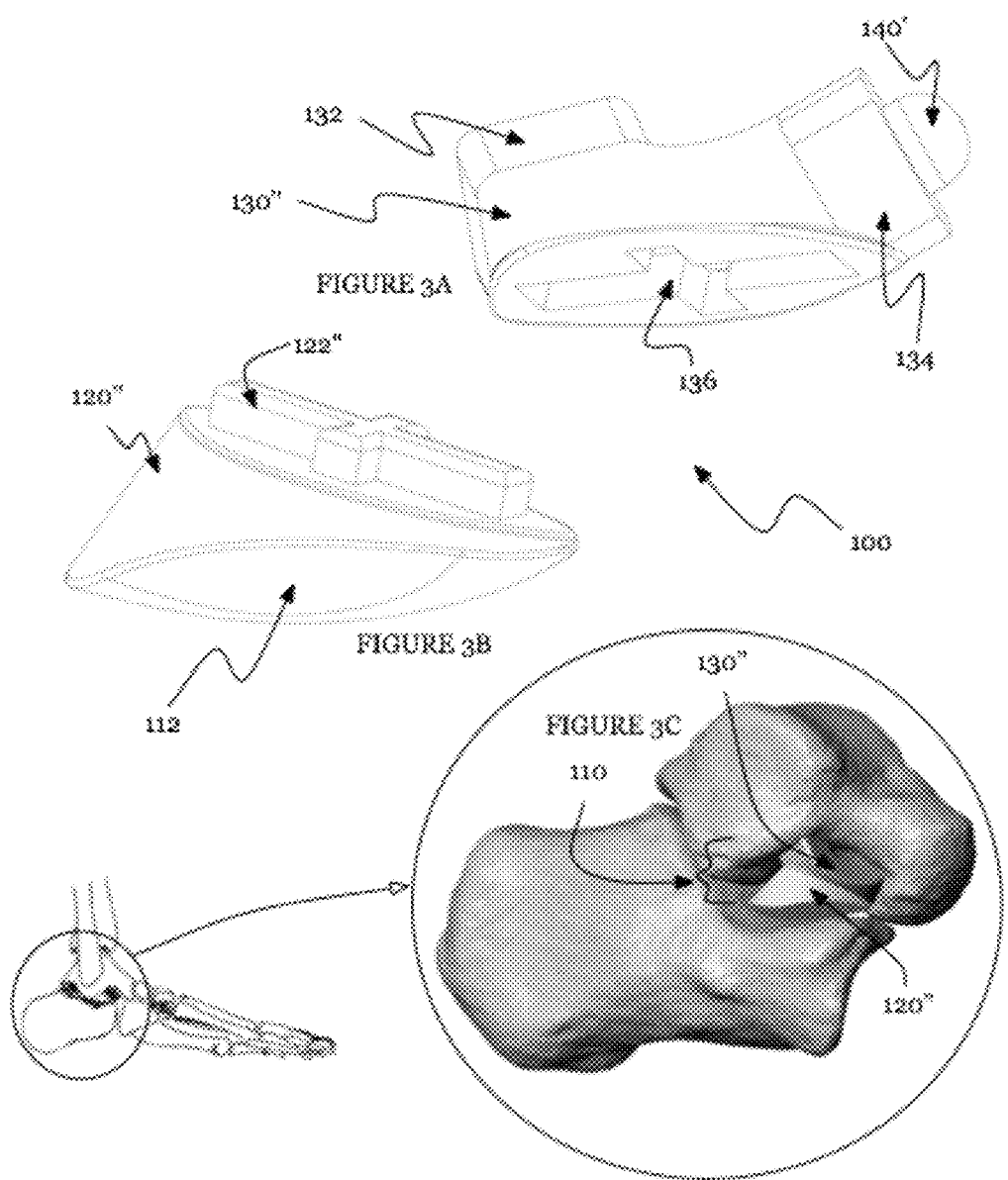

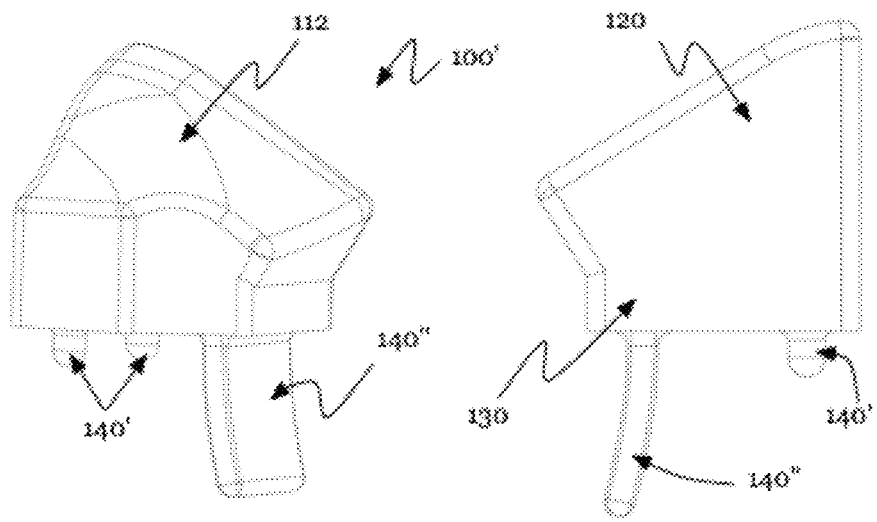
FIGURE 4A
FIGURE 4B
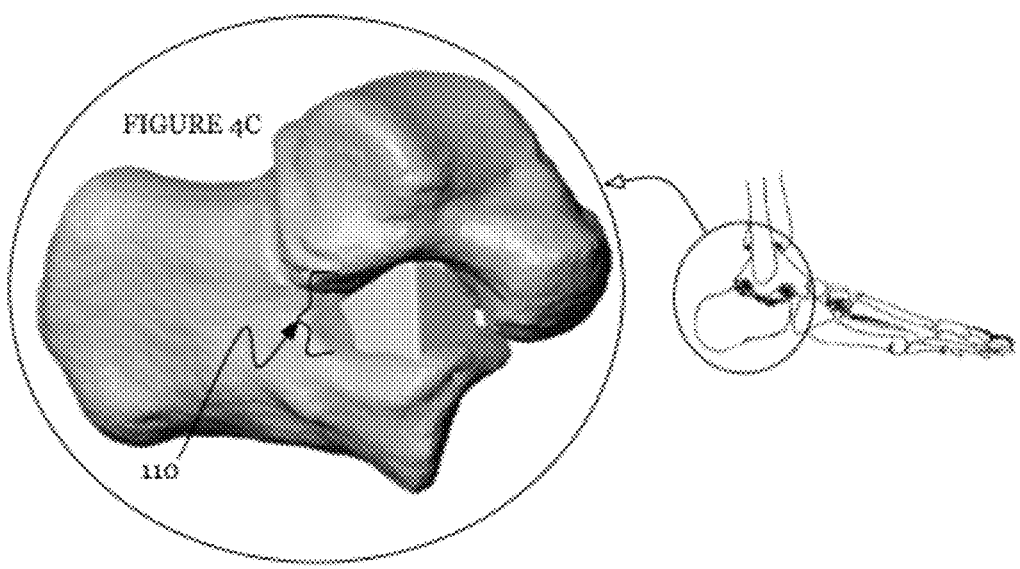
FIGURE 4C

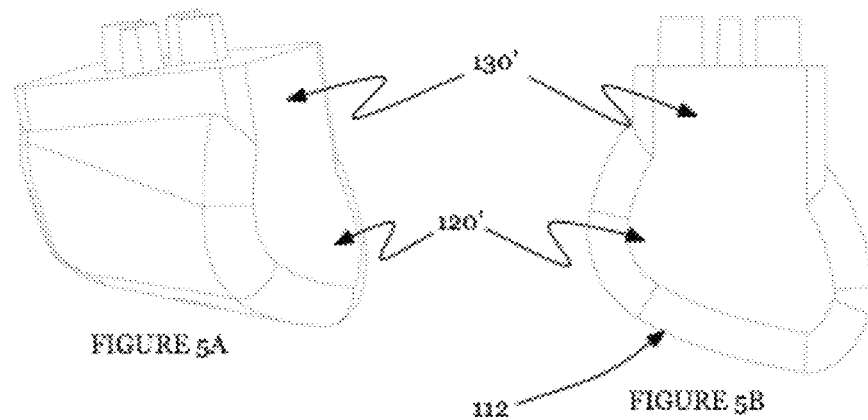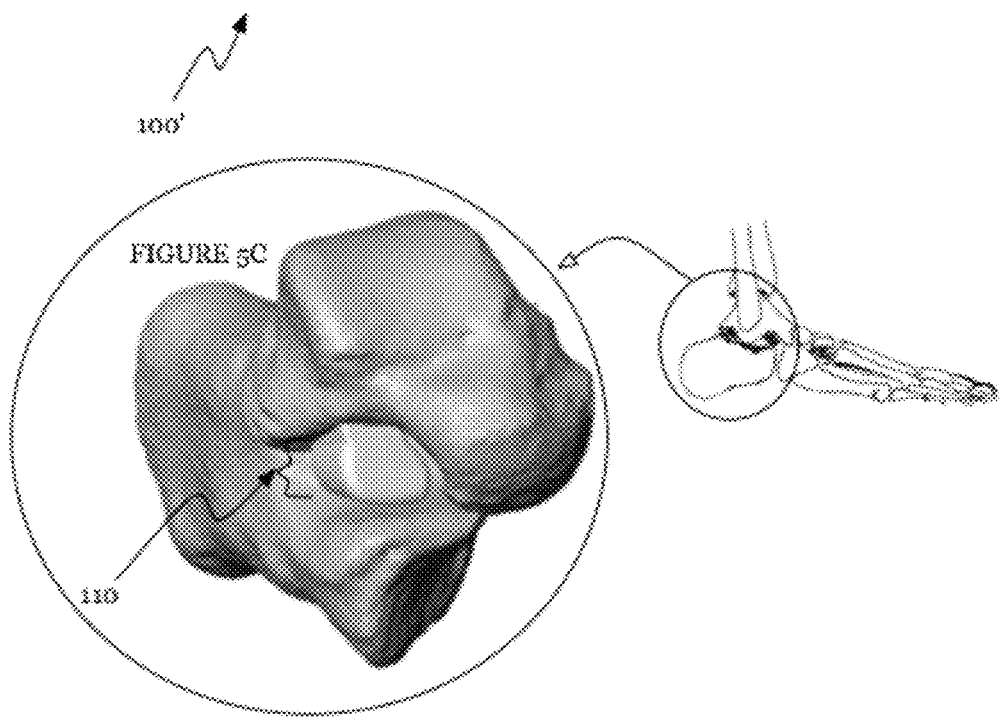

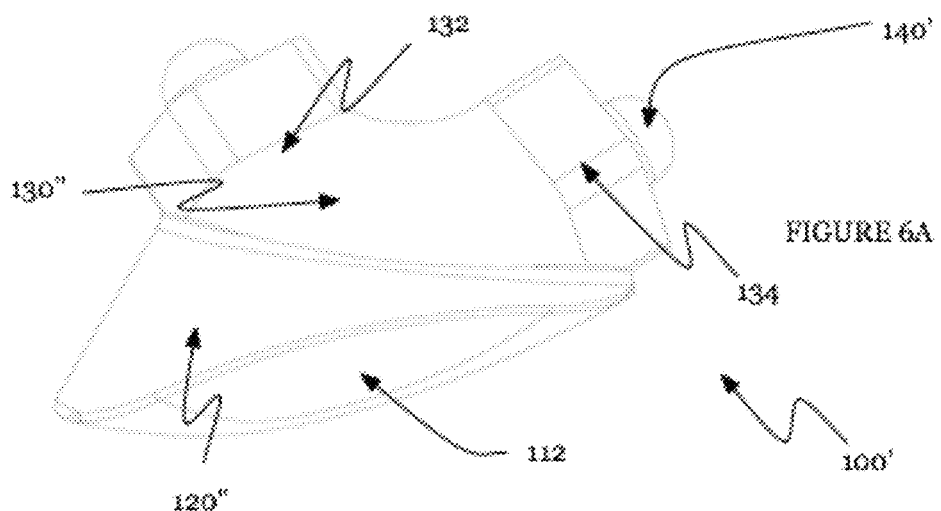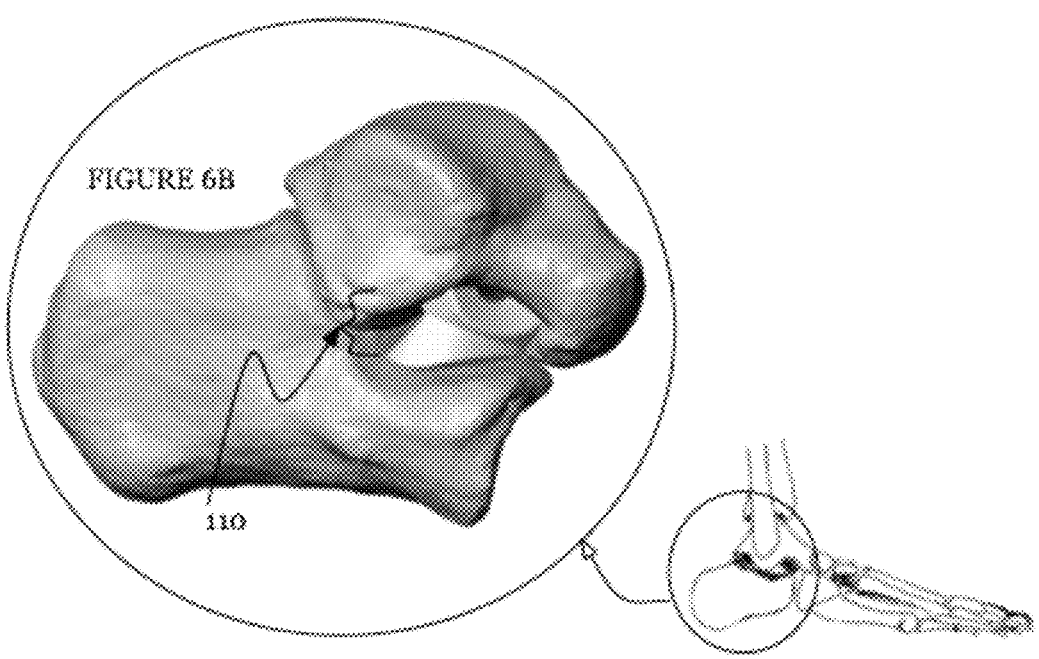

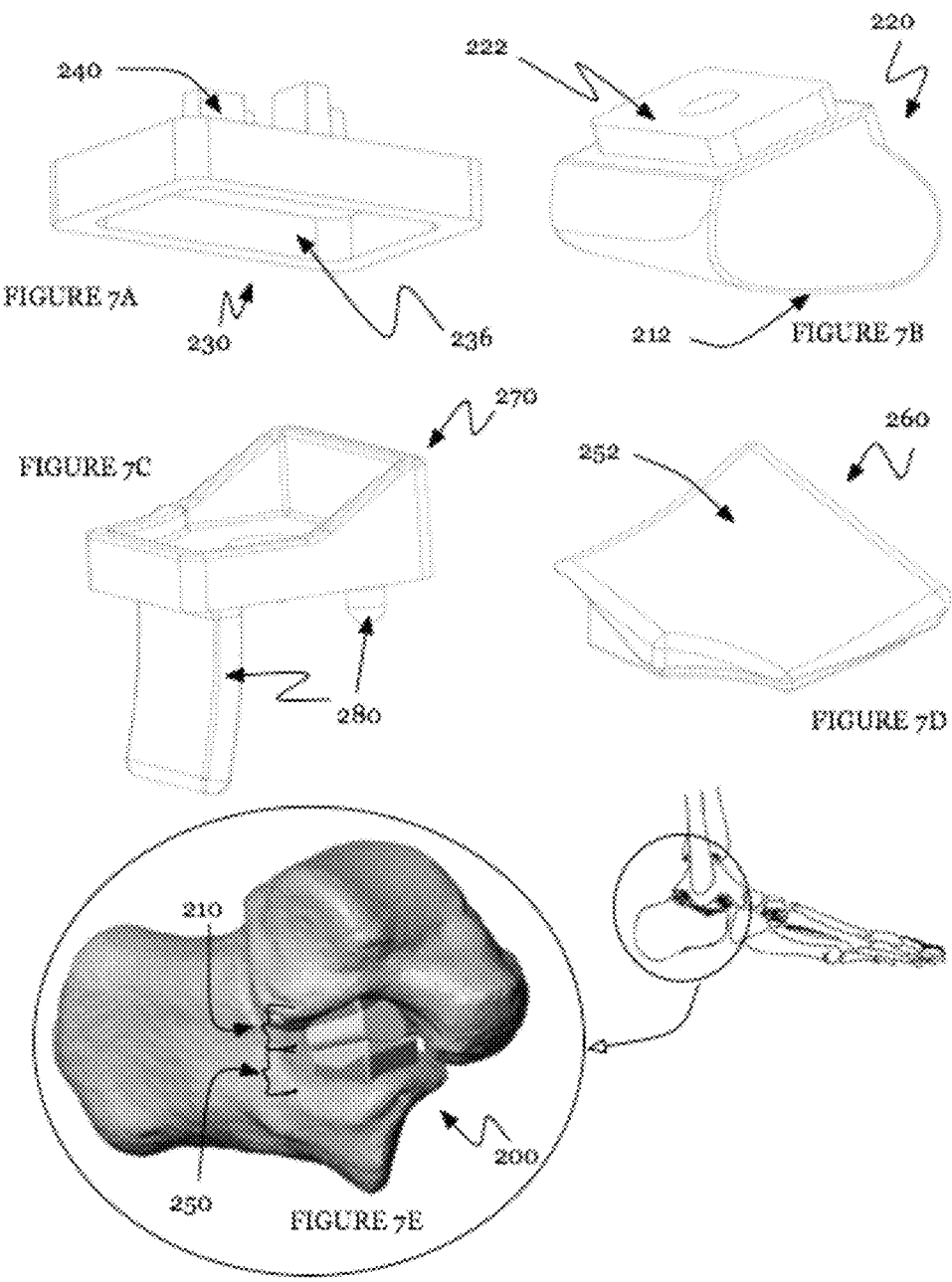

ized by the tension of ligaments located on the medial side of the talus and the posterior side of the calcaneus. When these ligaments fail due to either injury or disease, the talus is allowed to sublux or deviate from its normal position atop the calcaneus. This subluxation shifts the location of the calcaneus laterally (causing flatfoot), and allows the arch of the foot to collapse, increasing pronation. When this happens, the funnel shaped lateral opening of the sinus tarsi disappears.

SYSTEM AND METHOD FOR MODIFYING TALOCALCANEAL RELATIONSHIP IN A FOOT

CROSS-REFERENCE TO RELATED APPLICATIONS

Related Application Data

This application is a continuation of U.S. application Ser. No. 13/837,949, filed Mar. 15, 2013, hereby incorporated by reference.

TECHNICAL FIELD

This invention relates generally to the implant field, and more specifically to an improved subtalar implant in the arthroereisis field.

BACKGROUND

Hyperpronation and flat feet ("fallen arches") are relatively common conditions of the feet that cause pain, such as during sports or daily activities like walking. These conditions can be caused by collapse thru the sinus tarsi. The sinus tarsi is a space between the talus and the calcaneus. It is funnel shaped with the larger opening on the lateral side of the foot progressing across the foot to end in a small medial opening between the two aforementioned bones. This lateral opening or space between the bones is normally maintained by the tension of ligaments located on the medial side of the talus and the posterior side of the calcaneus. When these ligaments fail due to either injury or disease, the talus is allowed to sublux or deviate from its normal position atop the calcaneus. This subluxation shifts the location of the calcaneus laterally (causing flatfoot), and allows the arch of the foot to collapse, increasing pronation. When this happens, the funnel shaped lateral opening of the sinus tarsi disappears.

Common noninvasive treatments for hyperpronation and flat feet include the use of foot orthotics and shoe modifications. Situations in which these treatments fail to relieve symptoms may require implantation of a subtalar arthroereisis, a type of "bone block", in the sinus tarsi to "reopen" the collapsed sinus tarsi. The subtalar arthroereisis typically acts as a spacer to limit motion of the talus. However, after implantation of current subtalar arthroereisis systems, the arthroereisis often become loose within the sinus tarsi, causing painful irritation of the surrounding tissue. Furthermore, these systems are not stable enough to accurately reconstitute the anatomy of the sinus tarsi. Once the system fails, removal is mandatory, with resultant painful collapse and the need for a formal subtalar arthrodesis (joint fusion).

Thus, there is a need in the implant field to create an improved subtalar arthroereisis. This invention provides such an improved subtalar arthroereisis.

SUMMARY

Several exemplary systems for modifying the talocalcaneal relationship in a foot are described.

An exemplary system for modifying a talocalcaneal relationship in a foot comprises a first subtalar spacer, a first attachment member, a second attachment member, and a fastener. The first subtalar spacer comprises a first spacer mount portion and a first spacer body portion. The first spacer mount portion has a proximal end, a distal end, and a body that defines an implant surface, a second surface, a first side, a second side, a third side, a recess, a first aperture, a second aperture, a third aperture, and a bore. The implant surface is opposably facing the second surface. Each of the first side, second side, and third side extends from the implant surface to the second surface. The third side extends from the first side to the second side. The recess extends into the body of the first spacer mount portion from the second surface toward the implant surface to a recess base and from the proximal end of the first spacer mount portion toward the distal end of the first spacer mount portion to a recess distal end. The first aperture is defined on the first side and extends through the body of the first spacer mount portion and provides access to the recess. The second aperture is defined on second side and extends through the body of the first spacer mount portion and provides access to the recess. The third aperture is defined on the recess distal end and extends through the body of the first spacer mount portion and provides access to the recess. The bore extends through the recess base. The first spacer body portion has a body that defines an insert member, an intermediate member, an articulating member, and an aperture that extends through the body of the first spacer body portion. The insert member is disposed within the recess of the first spacer mount portion. The intermediate member is disposed between the insert member and the articulating member. The articulating member defines an articulating surface. The first attachment member is attached to the first spacer mount portion and has a body that defines a support member. The support member extends through the aperture defined by the first spacer body portion and is disposed within the third aperture of the first spacer mount portion. The second attachment member is attached to the first spacer mount portion. The second attachment member has a first end and a second end. The first end is disposed through the first aperture of the first spacer mount portion. The second end is disposed through the second aperture of the first spacer mount portion. The fastener is disposed through the bore of the first spacer mount portion and is adapted to attach the first spacer mount portion to a bone.

Additional understanding of the exemplary medical devices can be obtained by review of the detailed description, presented below, and the referenced drawings.

BRIEF DESCRIPTION OF THE FIGURES

FIGS. 1A and 1B are a perspective view and a side view, respectively, of a first variation of the spacer body portion of the subtalar spacer of the system.

FIG. 1C is a perspective view of a first variation of the spacer mount portion and the fastener of the system.

FIG. 1D is an anterior-lateral view of a variation of the system assembled and implanted in the sinus tarsi.

FIG. 2A is a perspective view of a second variation of the spacer mount portion and the fastener of the system.

FIGS. 2B and 2C are perspective views of a second variation of the spacer body portion of the subtalar spacer of the system.

FIG. 2D is an anterior-lateral view of a variation of the system assembled and implanted in the sinus tarsi.

FIGS. 3A and 3B are perspective views of another version of the second variations of the spacer mount portion and the spacer body portion, respectively, of the subtalar spacer of the system.

FIG. 3C is an anterior-lateral view of a variation of the system assembled and implanted in the sinus tarsi.

FIGS. 4A and 4B are perspective and side views, respectively, of the subtalar spacer and fastener of an alternative embodiment of the system.

FIG. 4C is an anterior-lateral view of an alternative embodiment of the system implanted in the sinus tarsi.

FIGS. 5A and 5B are perspective and side views, respectively, of the subtalar spacer and fastener of an alternative embodiment of the system.

FIG. 5C is an anterior-lateral view of an alternative embodiment of the system implanted in the sinus tarsi.

FIG. 6A is a side view of the subtalar spacer and fastener of an alternative embodiment of the system.

FIG. 6B is an anterior-lateral view of an alternative embodiment of the system implanted in the sinus tarsi.

FIGS. 7A through 7D are perspective views of a first spacer mount portion, first spacer body portion, second spacer mount portion, and second body portion, respectively, of another exemplary system.

FIG. 7E is an anterior-lateral view of the first and second subtalar spacers of an exemplary system implanted in the sinus tarsi.

DETAILED DESCRIPTION

Figure 8:
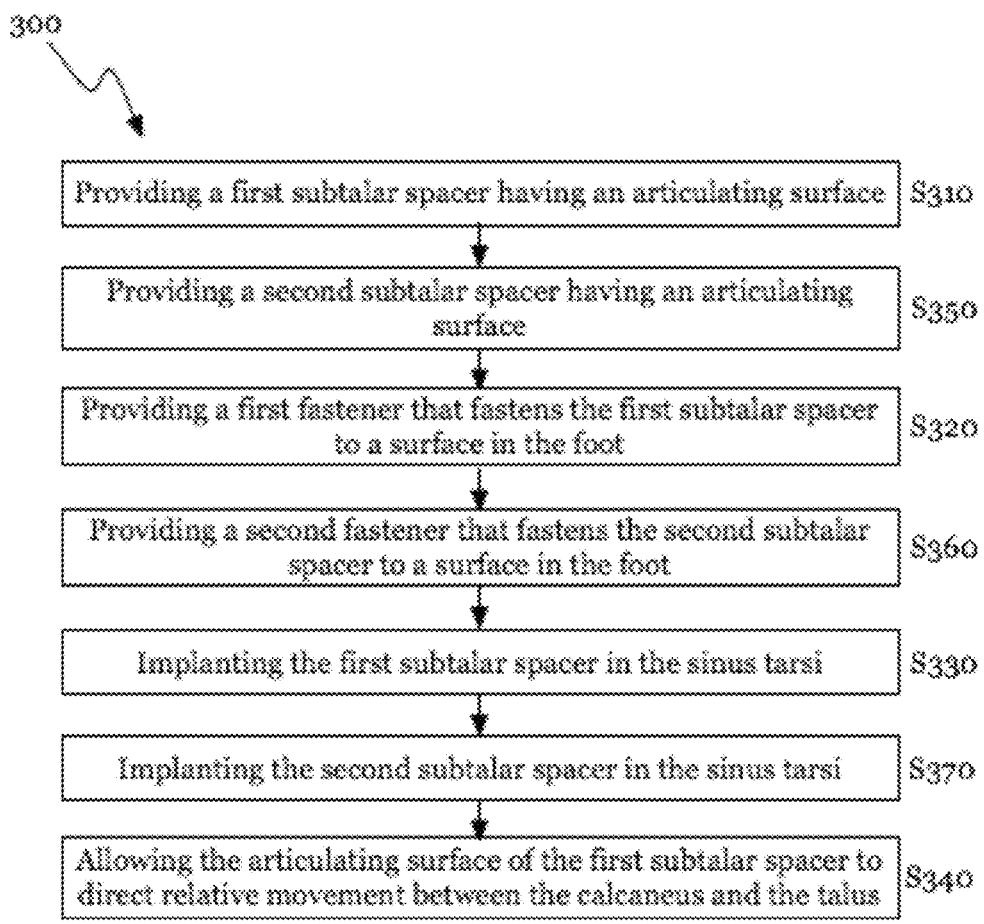
FIG. 8 is a schematic of an embodiment of the method for modifying talocalcaneal relationship in a foot.

The following detailed description and the appended drawings describe and illustrate various exemplary medical devices, systems, and methods. The description and drawings are exemplary in nature and are provided to enable one skilled in the art to make and use one or more exemplary medical devices, systems, and/or practice one or more exemplary methods. They are not limited to limit the scope of the claims in any manner.

The use of "exemplary" refers to "an example of and is not intended to convey meaning of an ideal or preferred embodiment. The use of "attached" refers to the fixed, releasable, or integrated association of two or more elements and/or devices. Thus, the term "attached" includes releasably attaching or fixedly attaching two or more elements and/or devices. As used herein, the terms "proximal" and "distal" are used to describe opposing axial ends of the particular element or feature being described.

As shown in FIGS. 1 through 7, the system 100 for modifying a talocalcaneal spatial relationship of the preferred embodiment includes a subtalar spacer 110 having an articulating surface 112, and a fastener 140 that fixes the subtalar spacer 110 to a bone surface in the foot, in which the articulating surface 112 of the subtalar spacer 110 directs relative movement between the calcaneus and the talus of the foot. The system 100 preferably restores a normal talocalcaneal spatial relationship by restoring the sinus tarsi in the foot and directing the compressive and sliding forces generated between the talus and calcaneus as the talus moves over the calcaneus during daily activities. The sliding motion creates a movable yet stable joint for reducing conditions caused by a collapsed sinus tarsi, including hyperpronation of the foot and flat feet.

The subtalar spacer 110 of the system 100 functions to restore the sinus tarsi space in a foot of a body. The subtalar spacer 110 is preferably implanted in the sinus tarsi of the foot and elevates (when the body is in a standing position) the talus bone relative to the calcaneus bone of the foot. The subtalar spacer 110 preferably includes an articulating surface 112, a spacer body portion 120, and a spacer mount portion 130.

The articulating surface 112 of the subtalar spacer 110 is preferably a surface on the spacer body portion 120 or any suitable portion of the subtalar spacer 110 that functions to direct forces between the talus and calcaneus as the talus moves over the calcaneus during daily activities. The articulating surface 112 preferably provides a surface for a bone, another spacer body portion, and/or any suitable tissue or surface to contact the subtalar spacer 110. As shown in FIGS. 1 through 7, the articulating surface 112 is preferably generally smooth to facilitate a sliding motion on the articulating surface 112, but may be ribbed, grooved, and/or have any suitable texture for articulating with another surface in any suitable articulating motion such a rolling and/or rubbing.

The spacer body portion 120 of the subtalar spacer 110 functions to provide structural support for the restoration of the sinus tarsi. The spacer body portion 120 may be one of several variations. In a first variation, as shown in FIGS. 1A through 1D, the spacer body portion 120 is adapted to be fixed to the calcaneus bone. As shown in FIGS. 1A and 1B, the spacer body portion 120 is preferably shaped to fill a significant portion of the sinus tarsi, and the articulating surface 112 is preferably contoured to articulate with an inferior surface of the talus bone. In particular, as shown in FIG. 1E, the articulating surface 112 is preferably on the superior side of the spacer body portion 120 and is gently sloped to articulate in a sliding motion with the anterior and/or lateral aspects of the inferior surface of the talus bone, but the articulating surface 112 may alternatively articulate with any suitable surface in any suitable motion. In a second variation, as shown in FIGS. 2A through 2D, the spacer body portion 120' is adapted to be fixed to the talus bone. As shown in FIGS. 2B and 2C, the spacer body portion is preferably shaped to fill a significant portion of the sinus tarsi, and the articulating surface 112 is preferably contoured to articulate with a superior surface of the calcaneus bone. In particular, as shown in FIG. 2D, the articulating surface 112 is preferably on the inferior side of the spacer body portion 120' and is sloped and contoured in a convex manner to articulate with a portion of the superior surface of the calcaneus bone in a sliding motion. Alternatively, as shown in FIGS. 3B and 3C, the articulating surface 112 on the spacer body portion 120" may be sloped and contoured in a concave manner to complement another portion of the superior surface of the calcaneus bone. However, the articulating surface 112 may articulate with any suitable surface in any suitable motion.

The spacer mount portion 130 of the subtalar spacer 110 functions to provide a surface for the fastener 140 to fasten the subtalar spacer 110 to a surface. By fastening the subtalar spacer 110 to a surface, the spacer mount portion 130 fixes the subtalar spacer 110 within the sinus tarsi, helping to promote bony ingrowth into the implant that reduces the likelihood of the subtalar spacer 110 loosening within the sinus tarsi and reduces pain. The spacer mount portion 130 may be one of several variations. In a first variation, as shown in FIGS. 1C and 1D, the spacer mount portion 130 is adapted to attach to the calcaneus bone. The inferior side of the spacer mount portion 130 preferably includes a generally flat planar surface for the fastener 140, which increases stability of the subtalar spacer 110 on the bone and simplifies surgical preparation for the implantation of the subtalar spacer 110. However, the inferior side of the spacer mount portion 130 may alternatively be curved, sloped, complementary to the natural contours of the calcaneus, a custom surgically prepared surface, or any suitable geometry. In a second variation, as shown in FIGS. 2A and 2D, the spacer mount portion is adapted to attach to the talus bone. The superior side of the spacer mount portion 130' is preferably similar to the inferior side of the spacer mount of the first variation, except that the superior side of the spacer mount portion of the second variation may be curved, sloped, complementary to the natural contours of the talus, or any suitable geometry. As shown in FIGS. 3A and 3C, the spacer mount portion 130" of the second variation may alternatively include a branch that has a first end 132 and a second end 134 that are adapted to attach to the talus bone. As shown in FIG. 3C, the multiple ends of the branch preferably provide additional mounting areas to improve fixation of the subtalar spacer 110 to the surface, and facilitate proper positioning of the alternative spacer body portion of the second variation to articulate with the calcaneus bone. The first end 132 is preferably a lateral end that is adapted to attach to a lateral portion of the inferior side of the talus, and the second end 134 is preferably a medial end that is adapted to attach to a medial portion of the anterior/inferior side of the talus. However, the first and second ends of the branch may alternatively be adapted to attach to any suitable portions of the talus and/or any suitable surface. Alternatively, the branch may include more than two ends, each of which is adapted to attach to a suitable individual portion of the talus or any other suitable surface.

The spacer body portion 120 and the spacer mount portion 130 are preferably separate components and the spacer body portion 120 is preferably coupled to the spacer mount portion 130. As shown in FIGS. 1 through 3, the spacer body portion 120 preferably includes a boss 122 and the spacer mount portion 130 preferably includes a recess 136, such that the boss 122 of the spacer body portion 120 couples to the recess 136 of the spacer mount portion 130. The boss of the spacer body portion 120 may have footprint of a square shape 122 as shown in FIG. 1B, a rectangular shape 122' as shown in FIG. 2C, a cross shape 122" as shown in FIG. 3B, circular, any suitable polygon, and/or any suitable shape. Alternatively, the spacer body portion may include a plurality of bosses. The spacer body portion 120 may include a key and the spacer mount portion 130 may include a keyway such that the spacer body portion and the spacer mount portion are restrained to couple in one orientation to help prevent accidental reversal or undesired orientations of the spacer body portion relative to the spacer mount portion. The spacer body portion 120 preferably couples to the spacer mount portion 130 in a permanent fashion, but may alternatively be semi-permanent and/or selectively removable to facilitate applications such as adapting to a growing and changing skeletal frame such as in a child, and obtaining a trial-and-error custom fit. The spacer body portion 120 preferably couples to the spacer mount portion 130 with a press-fit, but may alternatively and/or additionally couple to the spacer mount portion with cement, screws, bolts, and/or any suitable adhesive or fastener.

The spacer body portion 120 is preferably made of a durable, shock-absorbent and biocompatible material such as ultra high molecular weight polyethylene, but may alternatively and/or additionally be made of any suitable material. The spacer body portion is preferably made in an injection molding process, but may alternatively be made by milling, 3D printing, or any suitable manufacturing process. The spacer mount portion 130 is preferably made of a durable, biocompatible material such as titanium, but may alternatively and/or additionally be made of any suitable material. The spacer mount portion is preferably made in a casting or molding process, but may alternatively be made by milling or any suitable manufacturing process.

The subtalar spacer 110 may alternatively include multiple spacer body portions 120. As an example, the subtalar spacer 110 may include multiple spacer body portions 120 that couple to each other and/or to the spacer mount portion, in a puzzle-like fashion, and/or in a manner similar to that described above. Multiple spacer body portions 120 may be useful for some situations, such as swapping individual spacer body portions to obtain a custom fit.

In other alternatives, as shown in FIGS. 4 through 6, the spacer body portion 120 and the spacer mount portion 130 may alternatively be integrated into a single component. In these alternatives, the geometries of the spacer body portions and spacer mount portions are similar to those described above and shown in FIGS. 1 through 3. In particular, the subtalar spacer with integrated spacer body portion 120 and spacer mount portion 130 may be designed to be fixed to the calcaneus (FIG. 4), or to the talus (FIGS. 5 and 6).

The fastener 140 of the system 100 functions to fasten the subtalar spacer 110 to a bone surface in the foot. In particular, the fastener 140 preferably fastens the subtalar spacer 110 to the calcaneus bone or the talus bone. The fastener 140 may, however, fasten the subtalar spacer 110 to any suitable surface. The fastener 140 is preferably integrated into the spacer mount portion of the subtalar spacer 110, but may alternatively be a separate component and coupled to the spacer mount portion 130. The fastener 140 preferably fastens the subtalar spacer 110 to a bone surface by being inserted into the bone and promoting bony ingrowth into the system. The fastener 140 is preferably a protrusion in the shape of a peg 140' (as shown in FIGS. 1C and 3A), a tab 140" (as shown in FIG. 1C), a keel 140''' (as shown in FIG. 2A), and/or any suitable shape. However, the fastener 140 may alternatively and/or additionally include bone cement, screws, bolts, and/or any suitable adhesive or fastener. As shown in FIGS. 1C, 2A, and 3A, the fastener preferably includes a plurality of these structures, to anchor the subtalar spacer 110 to the bone. The fastener 140 may further include threads, bumps, notches, and/or any suitable texture to encourage bone growth for tissue fixation of the fastener within the bone, and may alternatively and/or additionally include bone growth factors to enhance bone growth. The fastener 140 is preferably inserted into the bone after the bone is surgically prepared, such as by leveling and/or drilling holes into the bone.

The fastener 140 is preferably made of a biocompatible material and through a manufacturing process similar to that of the spacer mount portion 130 of the subtalar spacer 110.

In a second preferred embodiment, as shown in FIGS. 7A through 7E, the system 200 includes a first subtalar spacer 210, a first fastener 240, a second subtalar spacer 250 and a second fastener 280. The first fastener 240 and second fastener 280 are preferably identical to the fastener 140 of the first preferred embodiment of the system 100. The first subtalar spacer 210 (which includes a first spacer body portion 220 and a first spacer mount portion 230) and second subtalar spacer 250 (which includes a second spacer body portion 260 and a second spacer mount portion 280) are preferably similar to the subtalar spacer 110 of the first preferred embodiment of the system 100, except as described below. As shown in FIG. 7E, the second subtalar spacer 250 is preferably adapted to be implanted in the sinus tarsi directly opposite the first subtalar spacer 210. The spacer body portions 220 and 260 of the first and second subtalar spacers, respectively, preferably are generally complementary and fill a significant portion of the sinus tarsi when implanted. The articulating surface 212 of the first subtalar spacer 210 preferably articulates with the articulating surface 252 of the second subtalar spacer 250. In the embodiment as shown in FIG. 7E, the articulating surfaces of the first and second subtalar spacers are preferably complementary to each other, such that the articulating surfaces 212 and 252 of the first and second subtalar spacers, respectively, articulate with each other in a sliding motion. However, the articulating surfaces of the first and second subtalar spacers may alternatively articulate with each other in a rolling, rubbing, or any suitable articulating motion. For example, as shown in FIG. 7E, a first subtalar spacer 210 may be implanted in the talus bone and a second subtalar spacer 250 may be implanted in the calcaneus bone, such that the articulating surface 212 of the first subtalar spacer 210 contacts the articulating surface 252 of the second subtalar spacer in a sliding manner. In this example, the articulating surfaces of the first and second subtalar spacers are made of ultra high molecular weight polyethylene for polyethylene-polyethylene articulating contact, which reduces the tendency of painful loosening of the first and second subtalar spacers. However, the articulating surfaces of the first and second subtalar spacers may alternatively be made of any suitable material, and be contoured in any suitable manner for articulation with each other.

As shown in FIG. 8, a method 300 for modifying a talocalcaneal spatial relationship in a foot in a body includes the steps of providing a first subtalar spacer having an articulating surface S310, providing a first fastener that fastens the subtalar spacer to a surface in the foot S320, implanting the first subtalar spacer in the sinus tarsi of the foot S330, and allowing the articulating surface of the first subtalar spacer to direct relative movement between the calcaneus and the talus of the foot S340. The method preferably restores a normal talocalcaneal spatial relationship by restoring the sinus tarsi in the foot, thereby reducing conditions caused by a collapsed sinus tarsi, including hyperpronation and flat feet.

The step of implanting the first subtalar spacer in the sinus tarsi of the foot S330 preferably includes preparing a surface and inserting the fastener into the bone surface. The surface is preferably on the calcaneus bone or the talus bone, but may alternatively be any suitable bone or any suitable surface. Preparing the surface is preferably similar to typical conventional preparation for surgical implantations and may include drilling, sanding, and/or other manipulations of the bone that are known to one ordinarily skilled in the art. Inserting the fastener into the bone surface preferably includes inserting a peg, tab, keel, or any suitable portion of the fastener into the bone surface. Alternatively, the step of implanting the first subtalar spacer in the sinus tarsi of the foot may include applying cement, or utilizing screws, bolts, and/or any suitable adhesive or fastener.

In one variation of the method, the step of allowing the articulating surface of the first subtalar spacer to direct relative movement between the calcaneus and the talus of the foot S340 preferably includes the step of allowing the articulating surface of the first subtalar spacer to articulate with a surface of the calcaneus. The articulation between the first subtalar spacer and the calcaneus is preferably a sliding motion, but may additionally and/or alternatively be a rolling, rubbing, and/or any suitable articulation. The sliding motion preferably helps direct forces between the talus and calcaneus as the talus moves over the calcaneus during daily activities, creating a movable yet stable joint. In this variation, the step of providing a fastener that fastens preferably includes providing a fastener that fastens the first subtalar spacer to the talus.

In another variation of the method, the step of allowing the articulating surface of the first subtalar spacer to direct relative movement between the calcaneus and the talus of the foot S340 preferably includes the step of allowing the articulating surface of the first subtalar spacer to articulate with a surface of the talus. The articulation between the first subtalar spacer and the calcaneus is preferably a sliding motion, but may additionally and/or alternatively be a rolling, rubbing, and/or any suitable articulation. The sliding motion preferably helps direct forces between the talus and calcaneus as the talus moves over the calcaneus during daily activities, creating a movable yet stable joint. In this variation, the step of providing a fastener that fastens preferably includes providing a fastener that fastens the first subtalar spacer to the calcaneus.

In another embodiment of the method, the method 300 preferably further includes the steps of providing a second subtalar spacer having an articulating surface S350, providing a second fastener that fastens the second subtalar spacer to a surface in the foot S360, and implanting the second subtalar spacer in the sinus tarsi of the foot S370. In this embodiment, the step of allowing the articulating surface of the first subtalar spacer to direct relative movement between the calcaneus and the talus of the foot S340 preferably includes allowing the articulating surface of the first subtalar spacer to articulate with the articulating surface of the second subtalar spacer.

Figure 9:
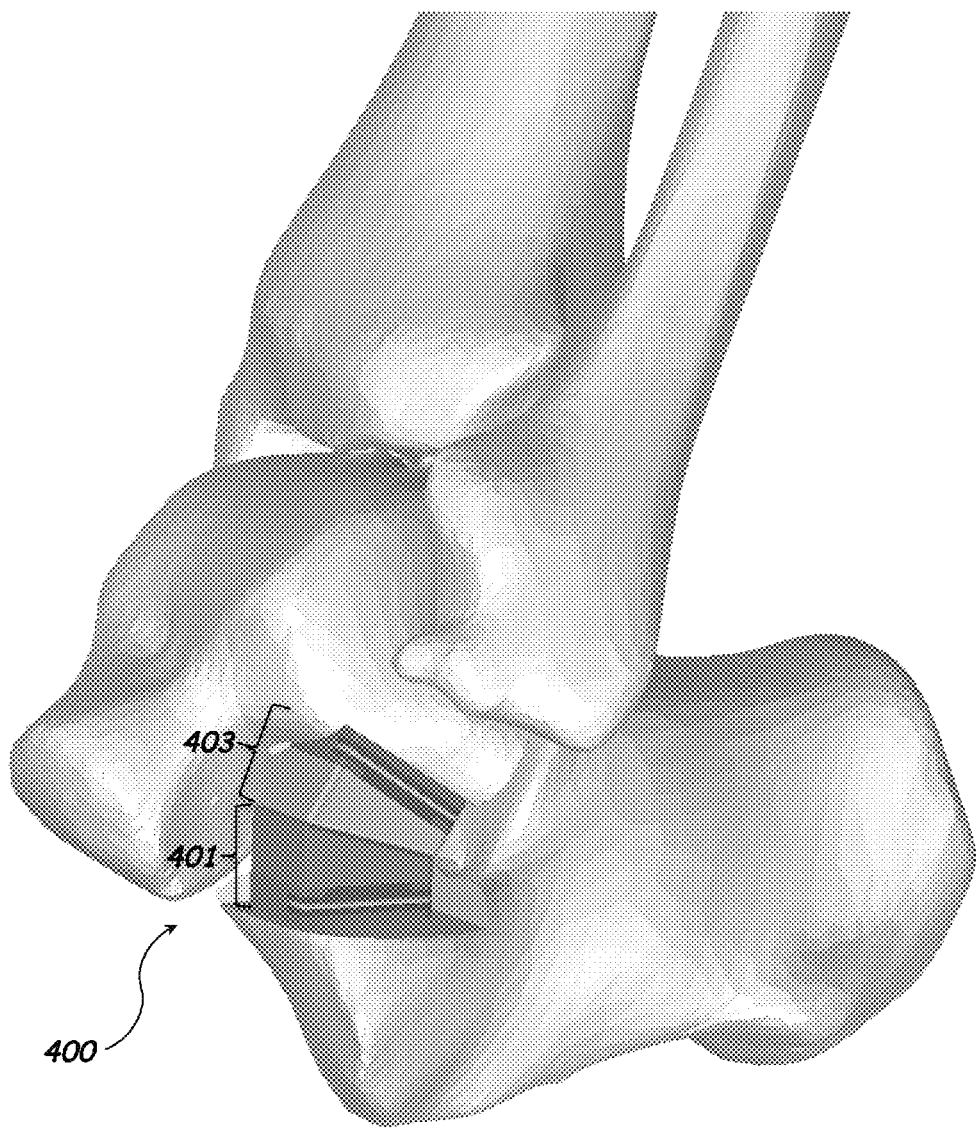
FIG. 9 is an anterior-lateral view of another first subtalar spacer and second subtalar spacer of an exemplary system implanted in the sinus tarsi.
Figure 10:
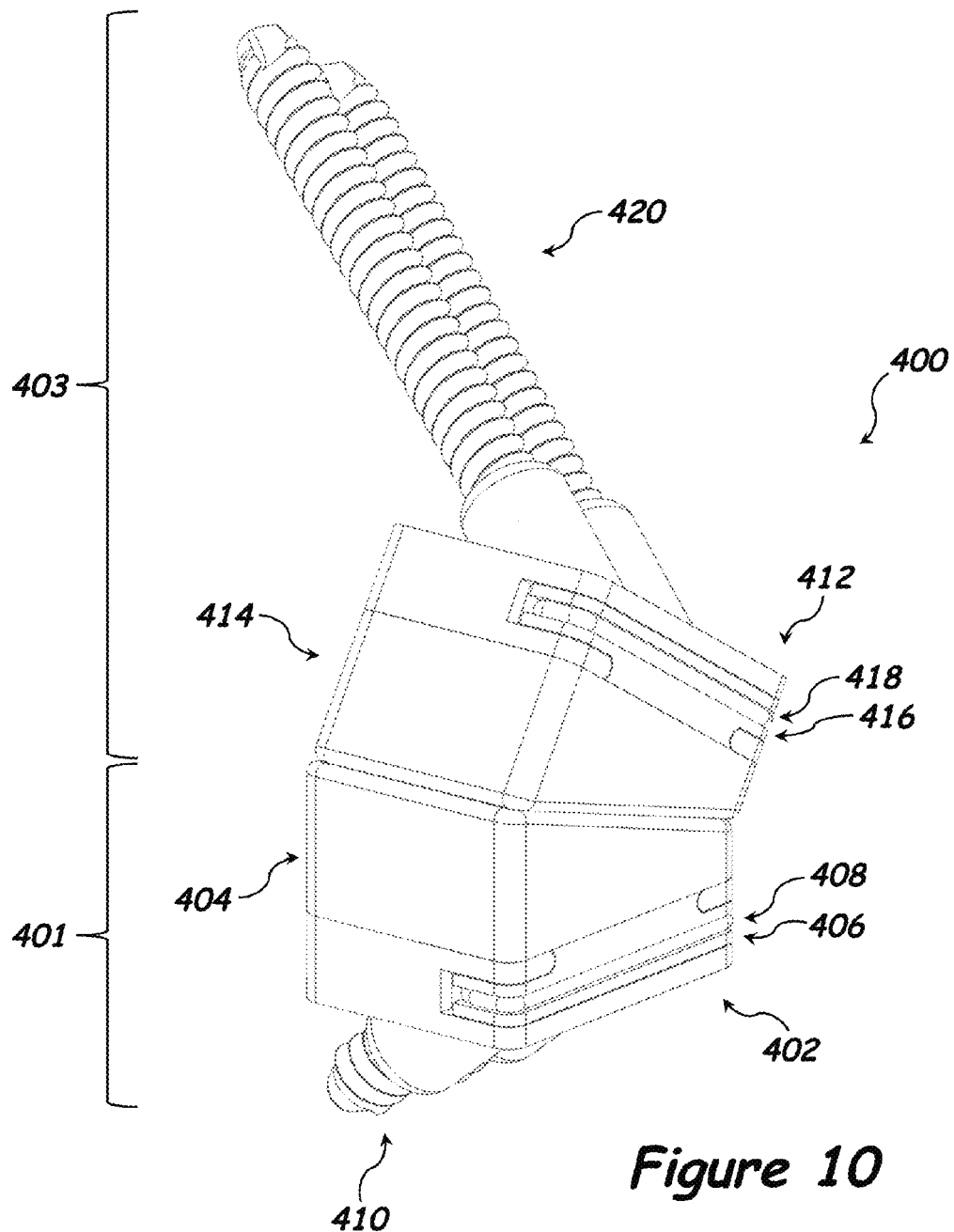
FIG. 10 is a perspective view of the system illustrated in FIG. 9 free of the sinus tarsi.
Figure 11:
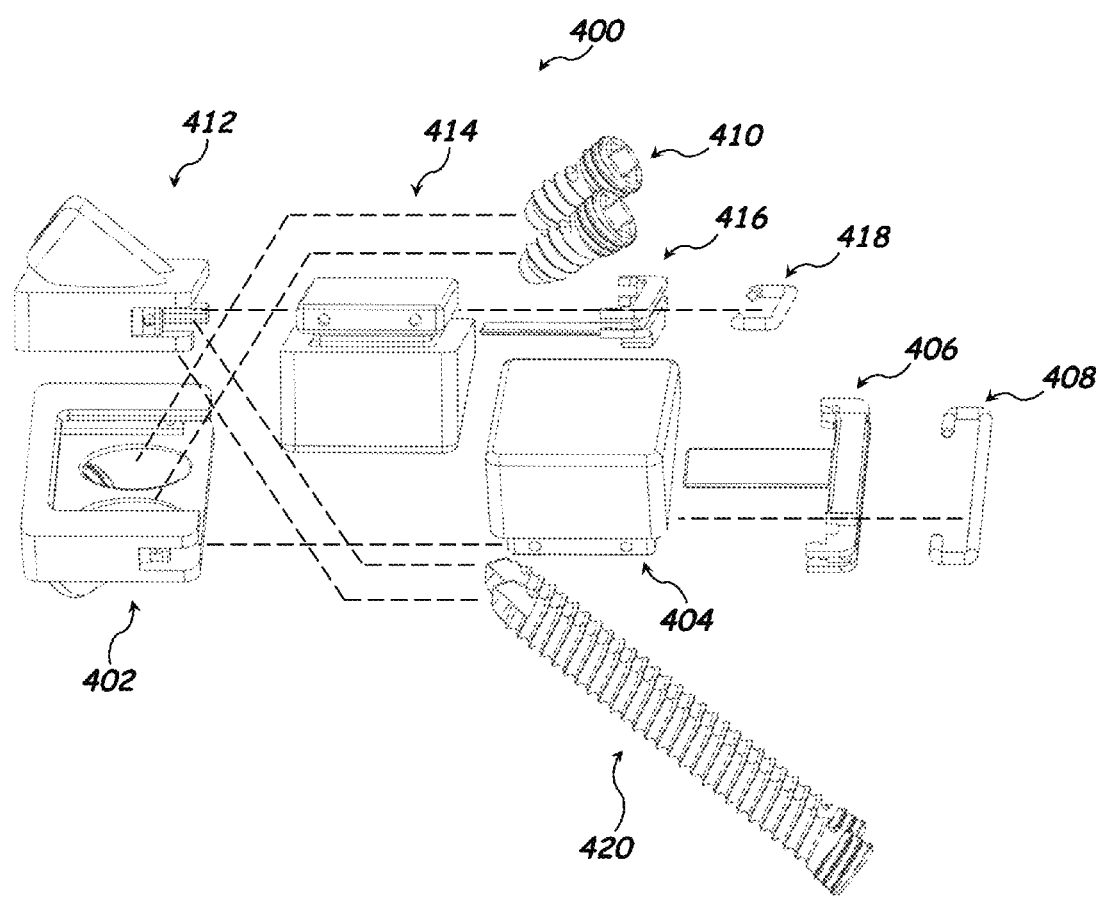
FIG. 11 is an exploded view of the system illustrated in FIG. 10.

FIG. 9 illustrates another subtalar spacer system 400 implanted in the sinus tarsi and FIGS. 10 through 23 illustrate the subtalar system 400 in FIG. 9 free of the sinus tarsi. In the illustrated embodiment, the subtalar system 400 comprises a first subtalar spacer 401 and a second subtalar spacer 403. The first subtalar spacer 401 comprises a first spacer mount portion 402, first spacer body portion 404, first attachment member 406, second attachment member 408, and a first plurality of fasteners 410. The second subtalar spacer 403 comprises a second spacer mount portion 412, second spacer body portion 414, third attachment member 416, fourth attachment member 418, and a second plurality of fasteners 420. First spacer body portion 404 is adapted to be attached to first spacer mount portion 402 using first attachment member 406 and second attachment member 408 and second spacer body portion 414 is adapted to be attached to second spacer mount portion 412 using third attachment member 416 and fourth attachment member 418, as described in more detail below.

In the illustrated embodiment, first spacer mount portion 402 and second spacer mount portion 412 are the same, except as described and illustrated herein. In addition, the first spacer body portion 404 and the second spacer body portion 414 are the same, except as described and illustrated herein.

Furthermore, the first attachment member 406 and the third attachment member 416 are the same, except as described and illustrated herein. Moreover, the second attachment member 408 and the fourth attachment member 418 are the same, except as described and illustrated herein. In the illustrated embodiment, reference numbers of the structural elements or features of the second spacer mount portion 412, second spacer body portion 414, third attachment member 416, and fourth attachment member 418 refer to the same structural element or feature of the first spacer mount portion 402, first spacer body portion 404, first attachment member 406, and second attachment member 408, offset by '.

The structural arrangement of the first spacer mount portion 402, first spacer body portion 404, first attachment member 406, and second attachment member 408, and similar second spacer mount portion 412, second spacer body portion 414, third attachment member 416, and fourth attachment member 418 is considered advantageous at least because it provides a mechanism for customizing an implant system for a particular implant site. For example, one or more first spacer body portions 404 and one or more second spacer body portions 414, each having a different structural configuration (e.g., articulating surface), or at least two having a different structural arrangement, can be provided to customize the system for a particular structural arrangement at an implant site.

The description provided below is illustrative of example structural arrangements for the first spacer mount portion 402, first spacer body portion 404, first attachment member 406, second attachment member 408, second spacer mount portion 412, second spacer body portion 414, third attachment member 416, and fourth attachment member 418. While particular structural arrangement have been illustrated and described, any suitable structural arrangement can be used, and skilled artisans will be able to select a suitable structural arrangement for a mount portion, body portion, first attachment member, and/or second attachment member according to a particular embodiment based on various considerations, including the material forming each component.

Figure 12:
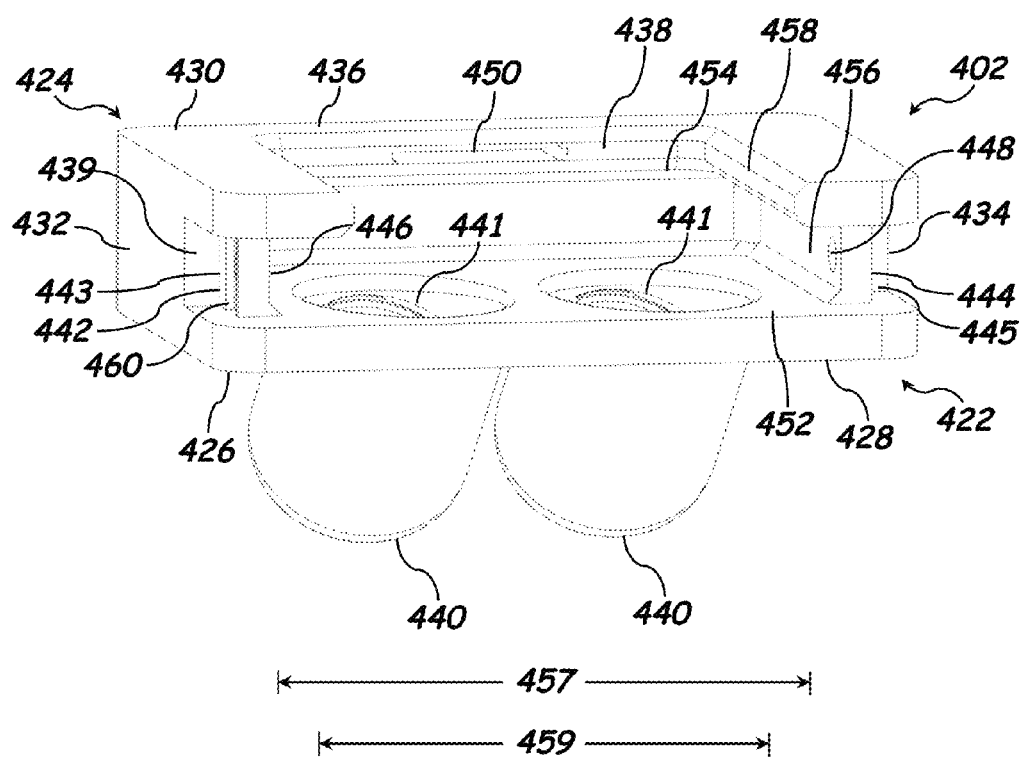
FIG. 12 is a perspective view of the first spacer mount portion of the system illustrated in FIG. 10.
Figure 13:
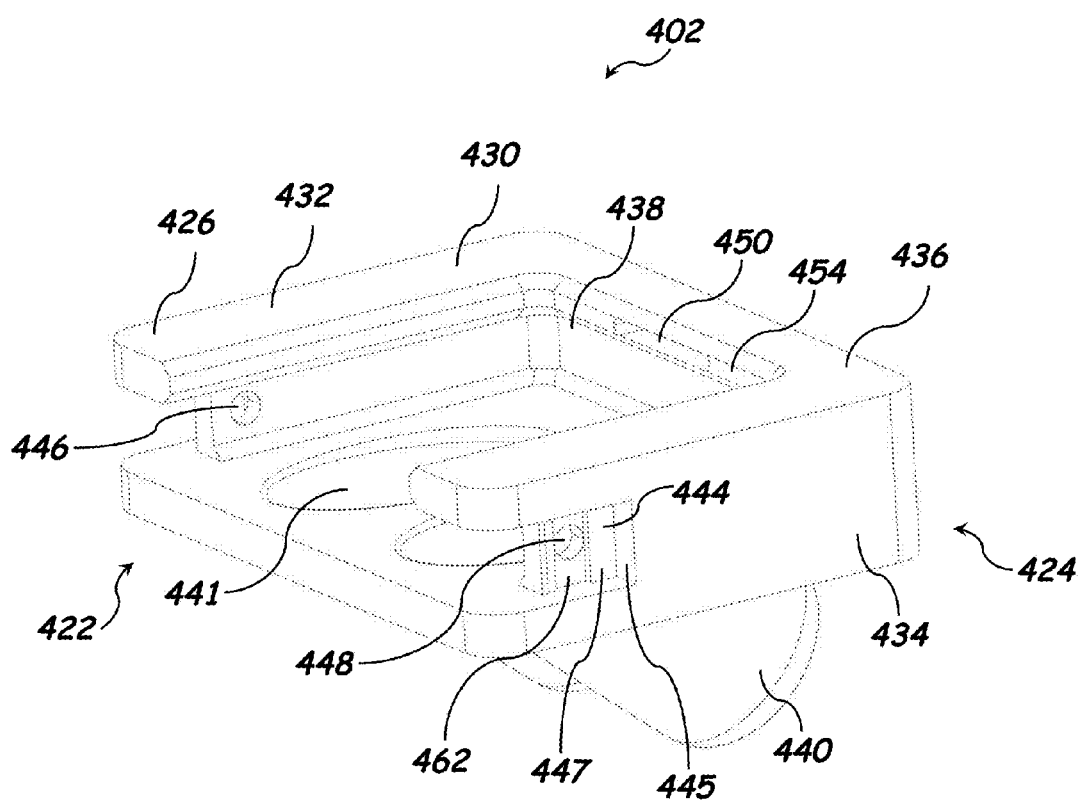
FIG. 13 is another perspective view of the first spacer mount portion of the system illustrated in FIG. 10.

FIGS. 12 and 13 illustrate the first spacer mount portion 402. The first spacer mount portion 402 has a proximal end 422, distal end 424, and a body 426 that defines a flat, or substantially flat, implant surface 428, second surface 430, first side 432, second side 434, third side 436, recess 438, plurality of protuberances 440, first notch 442, second notch 444, first aperture 446, second aperture 448, and third aperture 450.

Implant surface 428 is adapted to contact the bone, or surface, at an implant site and second surface 430 is opposably facing, or substantially opposably facing, implant surface 428. Each of the first side 432, second side 434, and third side 436 extends from the implant surface 428 to second surface 430. Third side 436 extends from the first side 432 to the second side 434.

Recess 438 is adapted to receive a portion, or the entirety, of first spacer body portion 404. Recess 438 extends into body 426 from second surface 430 to a recess base 452 and from the proximal end 422 toward the distal end 424 to a recess distal end 454 that is disposed proximal to distal end 424. Recess 438 has a first portion 456 and a second portion 458. First portion 456 has a first length 457 along proximal end 422 and second portion 458 has a second length 459 along proximal end 422. First length 457 is greater than second length 459.

Each protuberance of the plurality of protuberances 440 extends outward and away from implant surface 428 and toward distal end 424. Body 426 defines a bore 441 through each protuberance of the plurality of protuberances 440 that is adapted to receive a fastener from the first plurality of fasteners 410. The bore 441 of each protuberance of the plurality of protuberances 440 can have any structural configuration. For example, the bore 441 can be tapered, or include threads that mate with threads defined on a fastener of the first plurality of fasteners 410.

While a plurality of protuberances 440 and bores 441 has been illustrated, any suitable number of protuberances and bores can be included on a spacer mount portion, and skilled artisans will be able to select a suitable number of protuberances and bores according to a particular embodiment based on various considerations, including the type of attachment intended to be used between a mount portion and an implant surface (e.g., bone). Example number of protuberances and/or bores considered suitable to include on a mount portion include, but are not limited to, zero, one, at least one, two, a plurality, three, four, and any other number considered suitable for a particular application.

First notch 442 extends into body 426 from the proximal end 422 toward the distal end 424 to a first notch distal end 439 and from the first side 432 toward recess 438 to a first notch base 443. Body 426 defines a recess 460 on first notch base 443 that is adapted to receive a portion or first attachment member 406, as described in more detail herein. Second notch 444 extends into body 426 from the proximal end 422 toward the distal end 424 to a second notch distal end 445 and from the second side 434 toward recess 438 to a second notch base 447. Body 426 defines a recess 462 on second notch base 447 that is adapted to receive a portion or first attachment member 406, as described in more detail herein.

First aperture 446 is defined within recess 460 and extends through body 426 and provides access to recess 438. Second aperture 448 is defined within recess 462 and extends through body 426 and provides access to recess 438. Each of the first aperture 446 and second aperture 448 is adapted to receive a portion of second attachment member 408, as described in more detail below. Third aperture 450 extends through body 426 on recess distal end 454 and is adapted to receive a portion of first attachment member 406. Alternatively, third aperture 450 can comprise a second recess that extends into body 426 on recess distal end 454 that is adapted to receive a portion of first attachment member 406.

Each of the first aperture 446, second aperture 448, and third aperture 450 can have any suitable shape, and skilled artisans will be able to select a suitable shape for an aperture according to a particular embodiment based on various considerations, including the shape of a second attachment member. Example shapes considered suitable for a first aperture, second aperture, and/or third aperture include, but are not limited to, circular, oval, oblong, square, and any other shape considered suitable for a particular application. In the illustrated embodiment, the first aperture 446 and second aperture 448 are round and the third aperture 450 is elongated.

Figure 14:
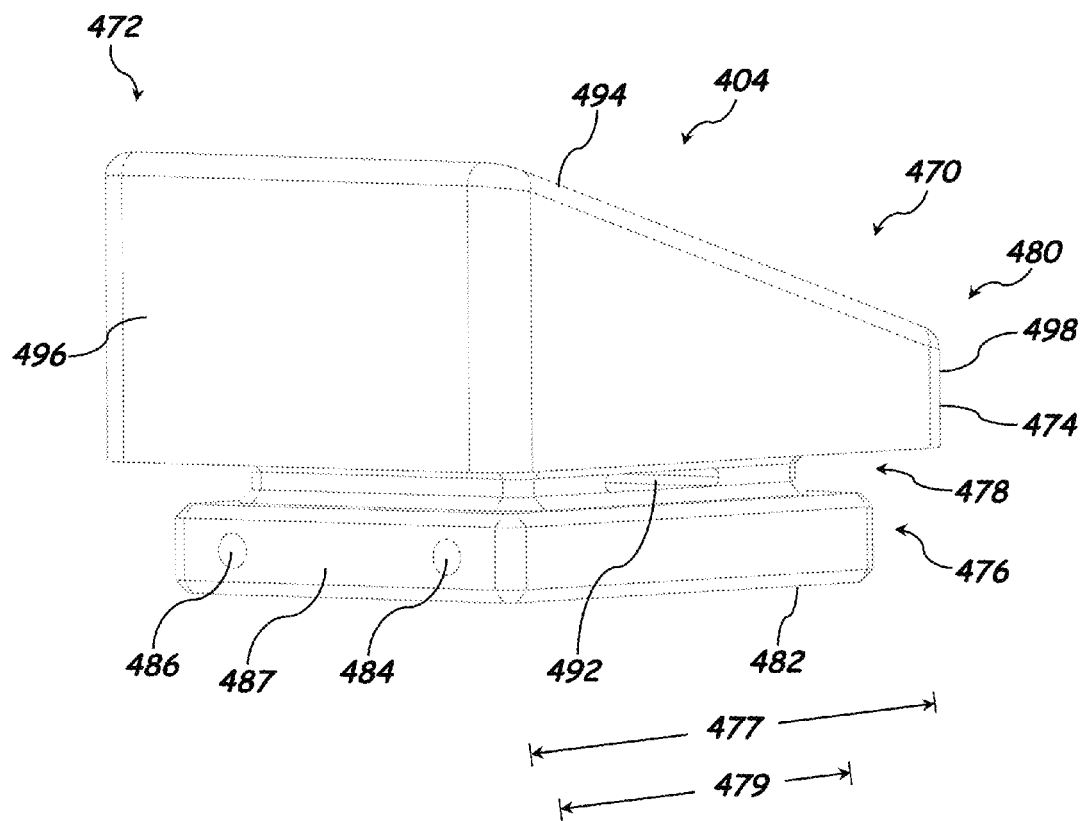
FIG. 14 is a perspective view of the first spacer body portion of the system illustrated in FIG. 10.
Figure 15:
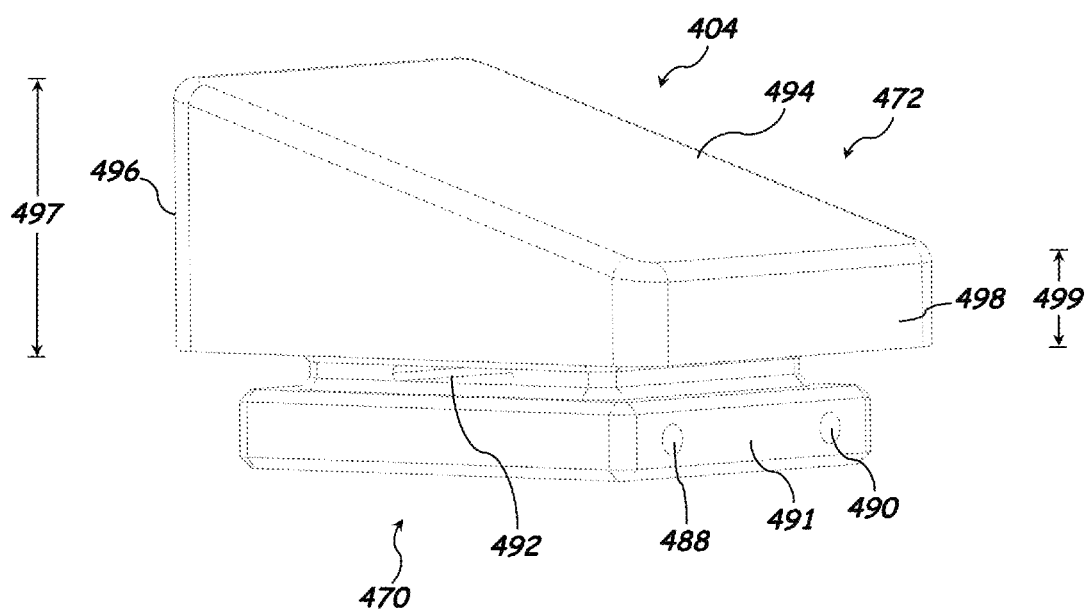
FIG. 15 is another perspective view of the first spacer body portion of the system illustrated in FIG. 10.
Figure 16:
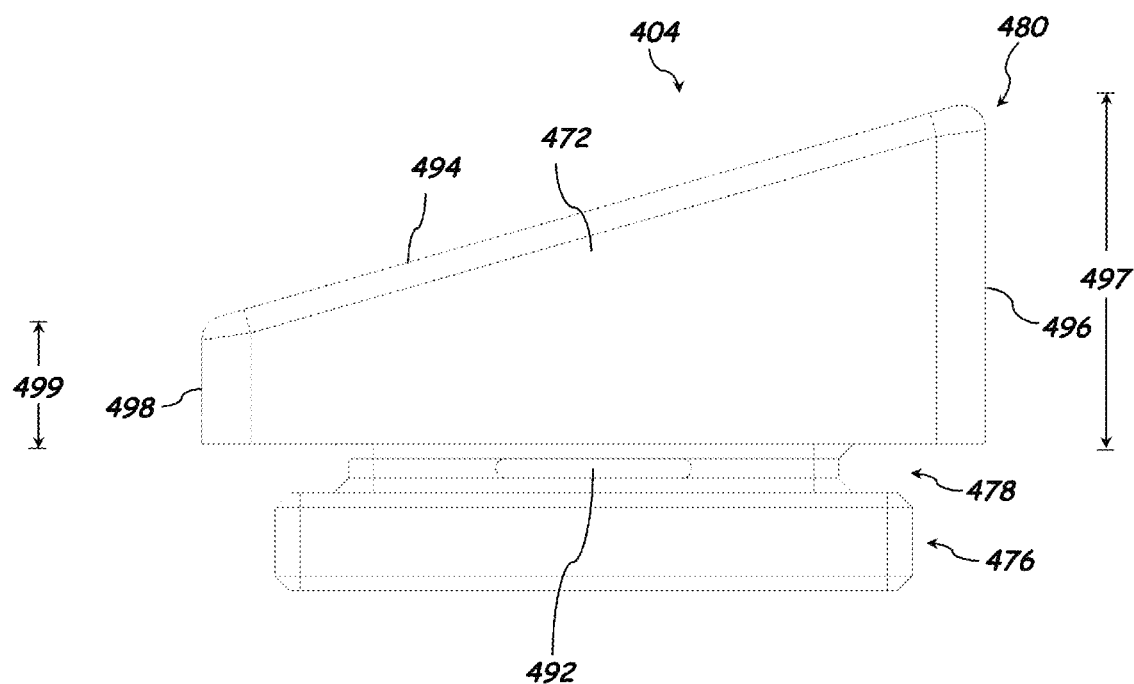
FIG. 16 is a side view of the first spacer body portion of the system illustrated in FIG. 10.

FIGS. 14, 15, and 16 illustrate the first spacer body portion 404. In the illustrated embodiment, first spacer body portion 404 is adapted to be attached to first spacer mount portion 402 and has a proximal end 470, distal end 472, and a body 474 that defines an insert member 476, intermediate member 478, and an articulating member 480.

Insert member 476 has a flat, or substantially flat, insert surface 482 and is adapted to be received by recess 438 (e.g., first portion 456) defined by first spacer mount portion 402. In FIG. 9 first spacer body portion 404 (e.g., insert member 476) is disposed within first spacer mount portion 402 (e.g., recess 438) Insert member 476 has a length 477 along the proximal end 470 that is equal to, substantially equal to, or less than, the length 457 of first portion 456 of recess 438. Body 474 defines a first recess 484 and a second recess 486 on a first side 487 of insert member 476 and a third recess 488 and fourth recess 490 on a second side 491 of insert member 476. Each of the first side 487 and second side 491 of insert member 476 extends from the proximal end 470 to the distal end 472 of insert member 476. Each of the first recess 484, second recess 486, third recess 488, and fourth recess 490 extends into the body 474 of insert member 476 and is adapted to receive a portion of second attachment member 408, as described in more detail herein.

While body 474 has been illustrated as defining first recess 484 and second recess 486 on first side 487 and third recess 488 and fourth recess 490 on second side 491, the body 474 of a spacer body portion can define any suitable number of recesses on a first side and/or second side. Skilled artisans will be able to select a suitable number of recess to define on a first side and/or second side of a spacer body portion according to a particular embodiment based on various considerations, including the structural arrangement of the spacer mount portion. Example number of recesses considered suitable to define a first side and/or second side of a spacer body portion include, but are not limited to, zero, one, at least one, two, a plurality, three, four, and any other number considered suitable for a particular application.

Intermediate member 478 extends from the insert member 476 to the articulating member 480 and is adapted to be received by recess 438 (e.g., second portion 458) defined by first spacer mount portion 402. Intermediate member 478 has a length 479 along proximal end 470 that is equal to, substantially equal to, or less than, the length 459 of second portion 458 of recess 438. Body 474 defines an aperture 492 that extends through first spacer body portion 404. In the illustrated embodiment, the aperture 492 extends through the intermediate member 478 from the proximal end 470 to the distal end 472 and is adapted to receive a portion of first attachment member 406, as described in more detail herein.

Articulating member 476 extends from the intermediate member 478 and away from insert member 476. Articulating member 480 has an articulating surface 494, first side 496, and a second side 498. Articulating surface 494 is adapted to articulate with the articulating surface 494' of second spacer body portion 414. First side 496 is opposably facing, or substantially opposably facing, second side 498 and each of the first side 496 and second side 498 extends from the proximal end 470 to the distal end 472 and from the intermediate member 478 to the articulating surface 494. First side 496 has a first length 497 that extends along the proximal end 470 and from the intermediate member 478 to the articulating surface 494. Second side 498 has a second length 499 that extends along the proximal end 470 and from the intermediate member 478 to the articulating surface 494. The first length 497 is greater than the second length 499. Thus, the articulating surface 494 tapers from the first side 496 to the second side 498.

While a particular structural arrangement of articulating surface 494 has been illustrated and described, any suitable structural arrangement can be used, and skilled artisans will be able to select a suitable structural arrangement for an articulating surface according to a particular embodiment based on various considerations, including the structural arrangement at an implant site. Example structural arrangements considered suitable include, but are not limited to, those described and/or illustrated herein, an articulating surface that tapers from a first side to a second side, an articulating surface that tapers from the proximal end to the distal end, an articulating surface that tapers from the proximal end to the distal end and from a first side to a second side, an articulating surface that tapers from a second side to a first side, an articulating surface that tapers from the distal end to the proximal end, an articulating surface that tapers from the distal end to the proximal end and from a second side to a first side, an articulating surface that is convex, an articulating surface that is concave, combinations of those described herein, and any other structural arrangement considered suitable for a particular application.

Figure 17:
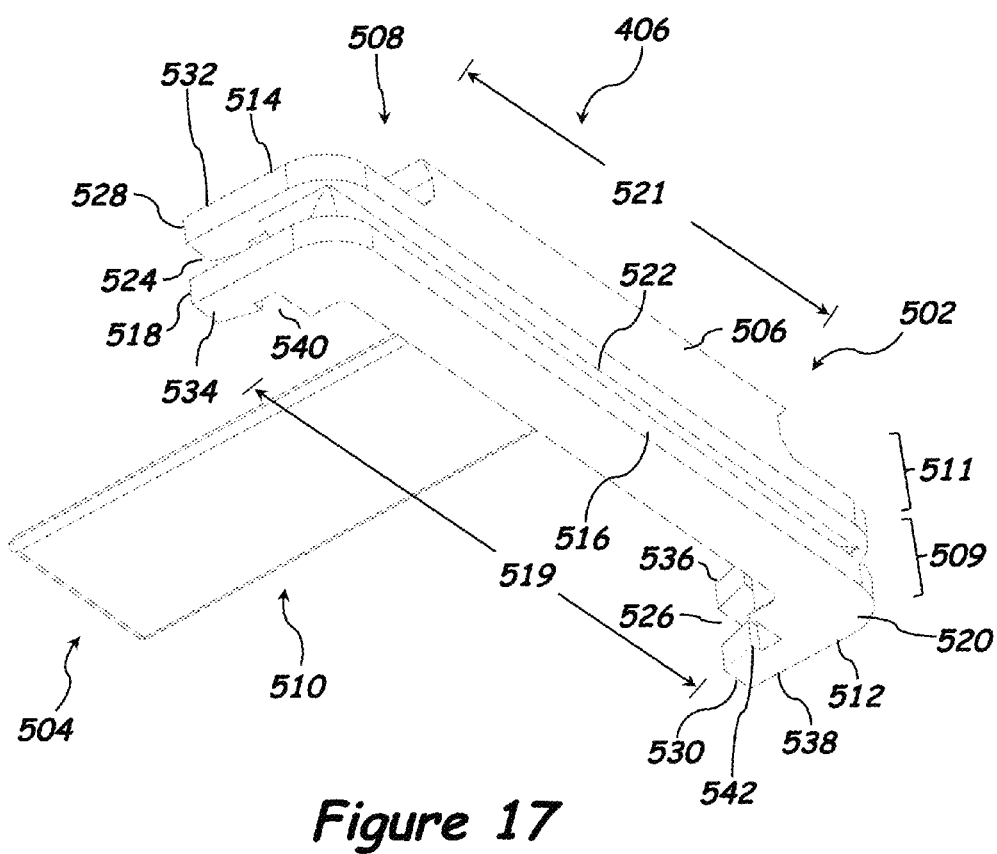
FIG. 17 is a perspective view of the first attachment member of the system illustrated in FIG. 10.
Figure 18:
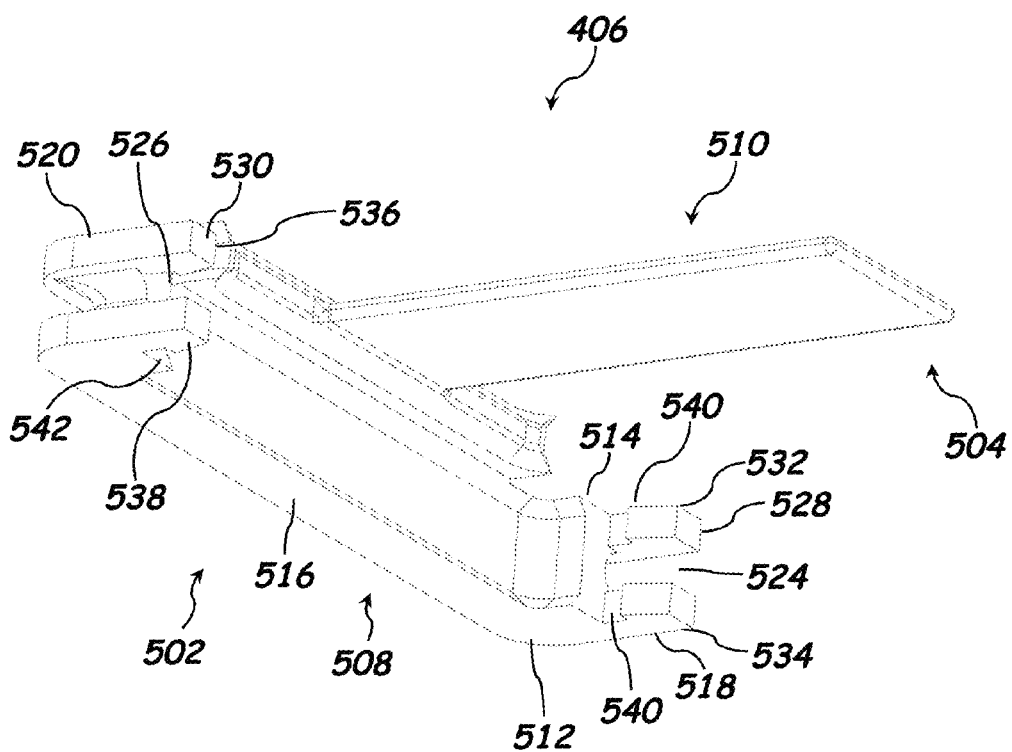
FIG. 18 is another perspective view of the first attachment member of the system illustrated in FIG. 10.

FIGS. 17 and 18 illustrate the first attachment member 406. First attachment member 406 is attached (e.g., releasably attached) to first spacer mount portion 402. Thus, first attachment member 406 is adapted to be attached to first spacer mount portion 402 such that upon attachment of first attachment member 406 to first spacer mount portion 402, first spacer body portion 404 is attached to first spacer mount portion 402. First attachment member 406 has a proximal end 502, distal end 504, and a body 506 that defines an engagement member 508 and a support member 510.

Engagement member 508 has a first portion 509 and a second portion 511. First portion 509 has a bottom surface 512, top surface 514, first side 516, second side 518, third side 520, recess 522, first notch 524, and a second notch 526. Each of the first side 516, second side 518, and third side 520 extends from the bottom surface 512 to the top surface 514. Each of the second side 518 and third side 520 extends from the first side 516 and toward the distal end 504. Second side 518 has a length that is less than, equal to, or substantially equal to, the distance from the proximal end 422 of the first spacer mount portion 402 to the first notch distal end 439 of the first spacer mount portion 402. Third side 520 has a length that is less than, equal to, or substantially equal to, the distance from the proximal end 422 of the first spacer mount portion 402 to the second notch distal end 445 of the first spacer mount portion 402. Second side 518 and third side 520 extend from first side 516 such that a length 519 of first side 516 disposed between the second side 518 and third side 520 is equal to, or substantially equal to, the length 457 of first portion 456 of recess 438. Second portion 511 extends from the top surface 514 of first portion 509 and away from the bottom surface 512 and has a length 521 along the proximal end 502 that is equal to, or substantially equal to, the length 459 of second portion 458 of recess 438.

Recess 522 extends into body 506 and along the first side 516, second side 518, and third side 520 and is adapted to receive a portion, or the entirety of, the second attachment member 408. First notch 524 extends through the distal end 528 of the first side 516 and between the bottom surface 512 and top surface 514. Second notch 526 extends through the distal end 530 of the second side 518 and between the bottom surface 512 and the top surface 514. When first attachment member 406 is attached to first spacer mount portion 402, first notch 524 is in communication with first aperture 446 of first spacer mount portion 402 and second notch 526 is in communication with second aperture 448 of first spacer mount portion 402.

Each of the second side 518 and third side 520 defines any suitable structure capable of attaching first attachment member 406 to first spacer mount portion 402. Any suitable structure and/or material capable of attaching a first attachment member 406 to a first spacer mount portion 402 is considered suitable, and skilled artisans will be able to select a suitable structure and/or material according to a particular embodiment based on various considerations, including the structure and material(s) forming a first spacer mount portion. Example structures and/or materials considered suitable to attach a first attachment member to a first spacer mount portion include, but are not limited to, adhesives, snap fit configurations, friction fit configurations, and any other structure and/or material considered suitable for a particular application.

In the illustrated embodiment, the second side 518 has a first arm 532 and a second arm 534 and the third side 520 has a first arm 536 and a second arm 538. Each of the first arm 532 and the second arm 534 of the second side 518 define a hook 540 on an inwardly facing surface that is adapted to engage with a proximal ridge defined by the recess 460 and first notch base 443 of the first spacer mount portion 402. Each of the first arm 536 and the second arm 538 of the third side 520 define a hook 542 on an inwardly facing surface that is adapted to engage with a proximal ridge defined by the recess 462 on second notch base 447 of the first spacer mount portion 402. This structural arrangement is considered advantageous at least because it provides a mechanism for fitting a first spacer mount portion with one or more first spacer body portions until a desired articulation between another spacer body portion or an implant site (e.g., bone) can be achieved.

Support member 510 extends from second portion 511 of engagement member 508 to distal end 504. Support member 510 is adapted to be passed through aperture 492 defined on intermediate member 478 of first spacer body portion 404 and disposed within third aperture 450 of first spacer mount portion 402.

Figure 19:
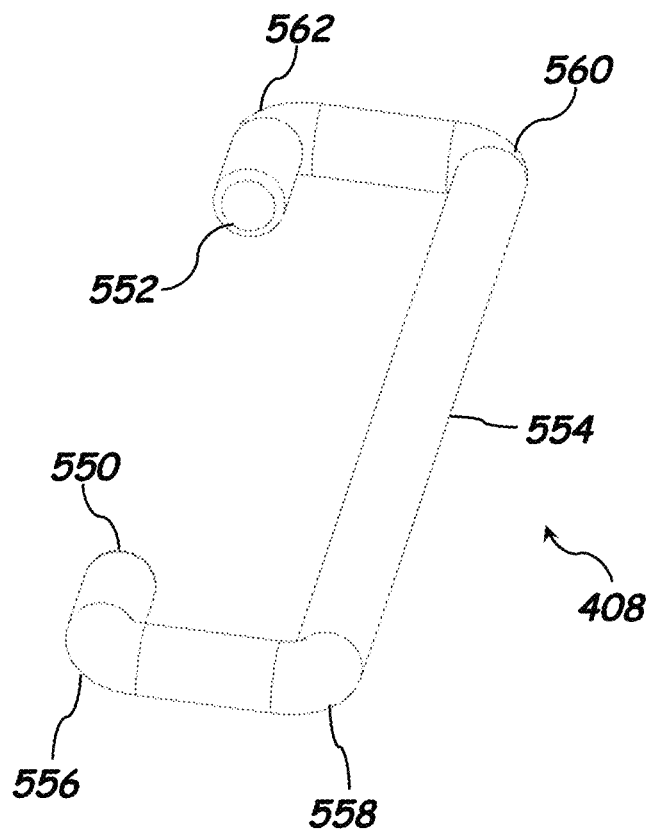
FIG. 19 is a perspective view of the second attachment member of the system illustrated in FIG. 10.
Figure 20:
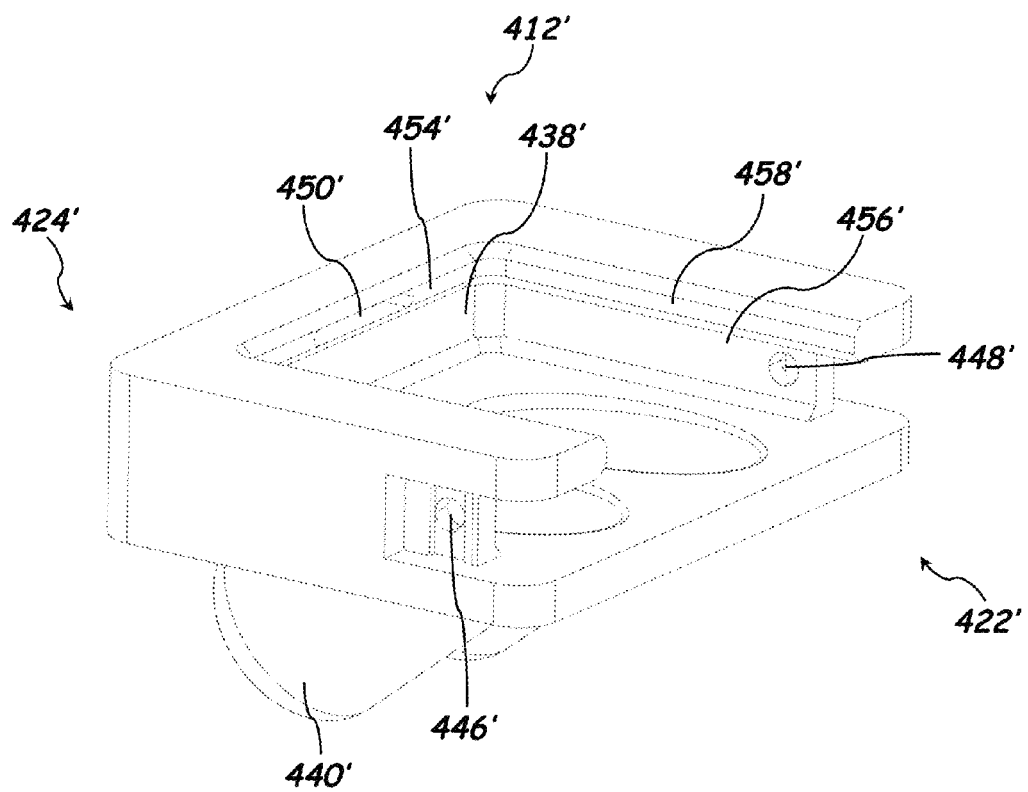
FIG. 20 is a perspective view of the second spacer mount portion of the system illustrated in FIG. 10.
Figure 21:
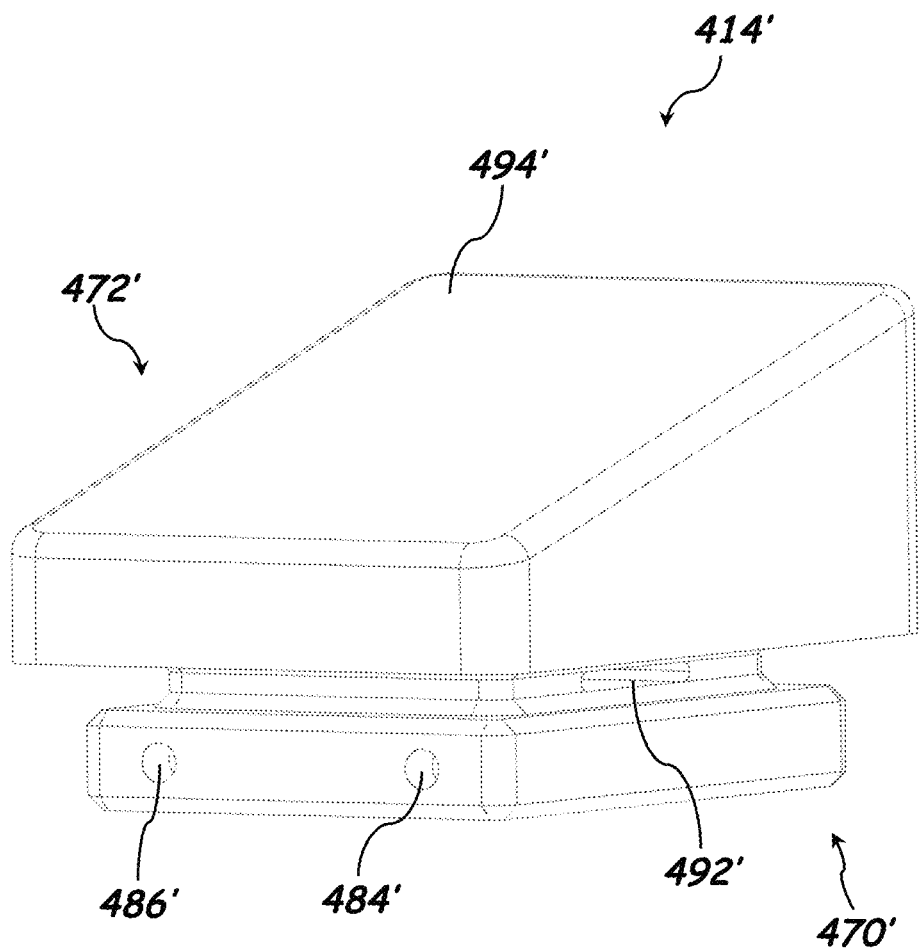
FIG. 21 is a perspective view of the second spacer body portion of the system illustrated in FIG. 10.
Figure 22:
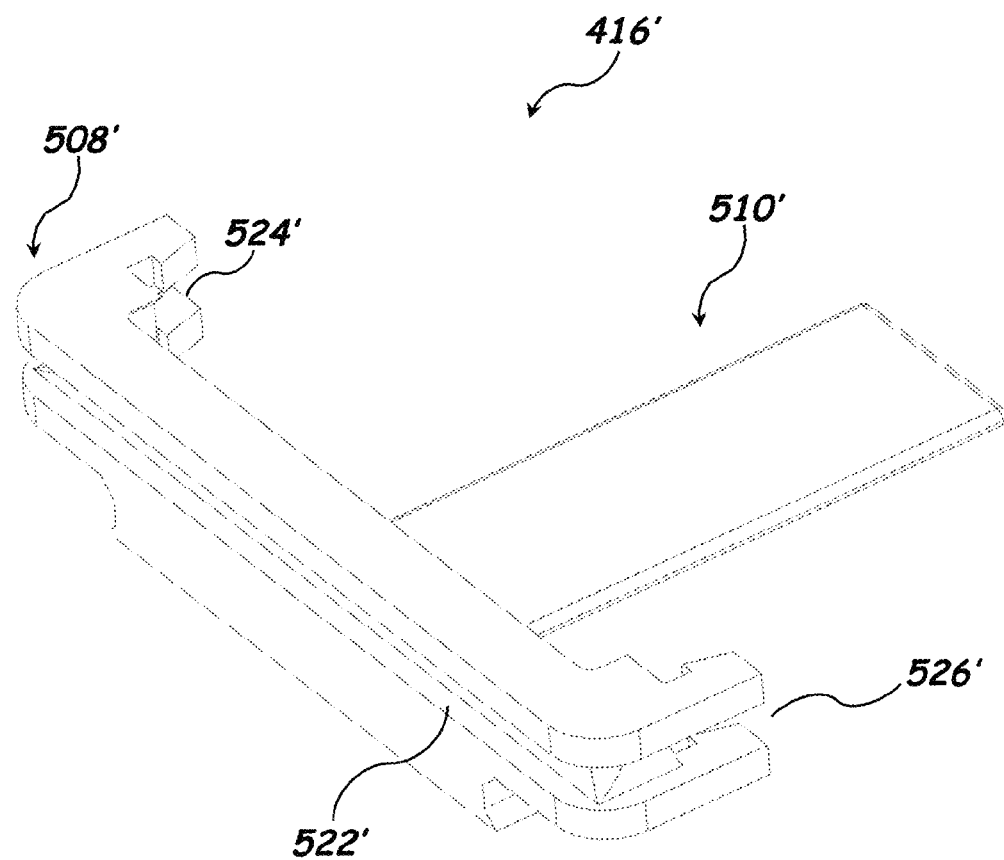
FIG. 22 is a perspective view of the third attachment member of the system illustrated in FIG. 10.
Figure 23:
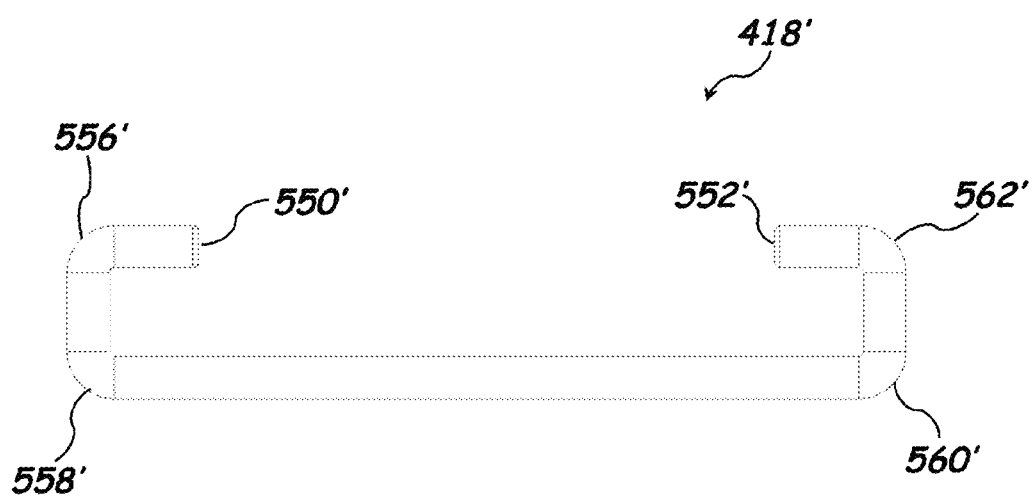
FIG. 23 is a top view of the fourth attachment member of the system illustrated in FIG. 10.

FIG. 19 illustrates the second attachment member 408. Second attachment member 408 is attached (e.g., releasably attached) to first spacer mount portion 402. Thus, second attachment member 408 is adapted to be received, or is disposed, within recess 522 of first attachment member 406 and attached to first spacer mount portion 402 such that upon attachment of second attachment member 408 to first spacer mount portion 402, first spacer body portion 404 is attached to first spacer mount portion 402 and first attachment member 406 is attached to first spacer mount portion 402.

Second attachment member 408 has a first end 550, second end 552, and an elongate body 554 that defines a first bend 556, second bend 558, third bend 560, and a fourth bend 562. The first bend 556 is defined between the first end 550 and the second bend 558 and defines an angle of 90 degrees, or substantially 90 degrees, between a portion of the elongate body 554 proximal to the first bend 556 and a portion of the elongate body 554 distal to the first bend 556. The second bend 558 is defined between the first bend 556 and the third bend 560 and defines an angle of 90 degrees, or substantially 90 degrees, between a portion of the elongate body 554 proximal to the second bend 558 and a portion of the elongate body 554 distal to the second bend 558. The third bend 560 is defined between the second bend 558 and the fourth bend 562 and defines an angle of 90 degrees, or substantially 90 degrees, between a portion of the elongate body 554 proximal to the third bend 560 and a portion of the elongate body 554 distal to the third bend 560. The fourth bend 562 is defined between the second end 552 and the third bend 560 and defines an angle of 90 degrees, or substantially 90 degrees, between a portion of the elongate body 554 proximal to the fourth bend 562 and a portion of the elongate body 554 distal to the fourth bend 562. A portion, or the entirety, of the first bend 556, second bend 558, third bend 560, and a fourth bend 562 is disposed on a plane that extends through elongate body 554.

In use, first spacer body portion 404 is inserted into recess 438 of first spacer mount portion 402. Support member 510 of first attachment member 406 is then passed through aperture 492 defined on first spacer body portion 404 and is disposed within third aperture 450 of first spacer mount portion 402. Second attachment member 408 is then disposed within recess 522 of first attachment member 406 such that the first end 550 passes through the first notch 524 of the first attachment member 406 and first aperture 446 of the first spacer mount portion 402 and is disposed within the first recess 484 of first spacer body portion 404 and the second end 552 passes through the second notch 526 of the first attachment member 406 and second aperture 448 of the first spacer mount portion 402 and is disposed within the third recess 488 of first spacer body portion 404. Second spacer mount portion 412, second spacer body portion 414, third attachment member 416, and fourth attachment member 418 are assembled similarly.

This structural arrangement is considered advantageous at least because it provides a mechanism for test fitting one or more first spacer body portions such that a desired articulation can be achieved. For example, as illustrated and described above, first spacer body portion 404 defines a first recess 484 and a second recess 486 on a first side 487 of insert member 476 and a third recess 488 and fourth recess 490 on a second side 491 of insert member 476. With this structural arrangement, a first spacer body portion 404 can be received by the first spacer mount portion 402 in one of two ways. For example, such that the distal end 472 of the first spacer body portion 404 is introduced first into the recess 438 of first spacer mount portion 402 and disposed at, or near, recess distal end 454 or such that the proximal end 470 of the first spacer body portion 404 is introduced first into the recess 438 of first spacer mount portion 402 and disposed at, or near, recess distal end 454. When the proximal end 470 is introduced first into recess 438, then the first end 550 of second attachment member 408 will be disposed within fourth recess 490 defined on first spacer body portion 404 and the second end 552 of the second attachment member 408 will be disposed within the second recess 486 defined on first spacer body portion 404.

The first plurality of fasteners 410 and second plurality of fasteners 420 can comprise any suitable fastener adapted to attach a mount portion to a structure (e.g., bone, implant site), and skilled artisans will be able to select a suitable fastener to include in the systems described herein according to a particular embodiment based on various considerations, including the structural arrangement of the mount portion. Example fasteners considered suitable include, but are not limited to, those described herein, screws, self-taping screws, and any other fastener considered suitable for a particular application. While a first plurality of fasteners 410 and a second plurality of fasteners have been illustrated, any suitable number of fasteners can be included in a system, and skilled artisans will be able to select a suitable number of fasteners to include according to a particular embodiment based on various considerations, including the number of protuberances and/or bores defined by a spacer mount portion. Example number of fasteners considered suitable to include in a system include, but are not limited to, one, at least one, two, three, four, five, six, and any other number considered suitable for a particular application.

In the illustrated embodiment, each fastener of the first plurality of fasteners 410 has a first length and each fastener of the second plurality of fasteners 420 has a second length. The second length is greater than the first length. The length of a fastener can be determined based on at least the structure at an implant site (e.g., the thickness of the bone). Each fastener of the first plurality of fasteners 410 is adapted to pass through, or be disposed within, a bore 441 defined on first spacer mount portion 402 such that it attaches first spacer mount portion 402 at an implant site (e.g., bone, talus, calcaneus). Each fastener of the second plurality of fasteners 420 is adapted to pass through, or be disposed within, a bore 441' defined on second spacer mount portion 412 such that it attaches second spacer mount portion 412 at an implant site (e.g., bone, talus, calcaneus).

When implanted at an implant site, the first spacer mount portion 402 is attached to a first bone (e.g., talus, calcaneus) and the second spacer mount portion 412 is attached to a second bone that is different from the first bone (e.g., calcaneus, talus). The articulating surface 494 of first spacer body portion 404 is adapted to articulate with the articulating surface 494' of the second spacer body portion 412. The articulating surface 494 of the first spacer body portion 404 can be the same as, or different from, the articulating surface 494' of the second spacer body portion 414.

While a first spacer mount portion 402, first spacer body portion 404, first attachment member 406, second attachment member 408, and a first plurality of fasteners 410 has been illustrated and described as provided with a second spacer mount portion 412, second spacer body portion 414, third attachment member 416, fourth attachment member 418, and a second plurality of fasteners 420, a first spacer mount portion 402, first spacer body portion 404, first attachment member 406, second attachment member 408, and a first plurality of fasteners 410 can be provided independent of, or implanted independent of, a second spacer mount portion 412, second spacer body portion 414, third attachment member 416, fourth attachment member 418, and a second plurality of fasteners 420.

As a person skilled in the art will recognize from the previous detailed description and from the figures and claims, modifications and changes can be made to the preferred embodiments of the invention without departing from the scope of this invention defined in the following claims.

The invention claimed is:

1. A method for modifying a talocalcaneal relationship in a foot comprising implanting a subtalar spacer system within said foot, wherein said implanted subtalar spacer system comprises:
    a first subtalar spacer comprising:
        a first spacer mount portion having a body defining a recess and a bore, the recess extending into the body of the first spacer mount portion and the bore extending through the body of the first spacer mount portion;
        a first spacer body portion having a body that defines an insert member, articulating member, and an aperture that extends through the body of the first spacer body portion, the insert member disposed within the recess of the first spacer mount portion, the articulating member of the first spacer body portion defining an articulating surface;
        a first attachment member attached to the first spacer mount portion, the first attachment member having a body that defines a support member that extends through the aperture defined by the first spacer body portion;
        a second attachment member attached to the first spacer mount portion wherein the second attachment member has a first end and a second end; and
        a first fastener disposed through the bore of the first spacer mount portion and attaching the first spacer mount portion to a bone within said foot.

2. The method of claim 1, wherein said first spacer mount portion has a proximal end, a distal end, and said body defines an implant surface, a second surface, a first side, a second side, a third side, said recess, a first aperture, a second aperture, a third aperture, and said bore.

3. The method of claim 2, wherein the implant surface opposably faces the second surface, each of the first side, second side, and third side extend from the implant surface to the second surface, the third side extends from the first side to the second side, the recess extends into the body of the first spacer mount portion from the second surface toward the implant surface to a recess base and from the proximal end of the first spacer mount portion toward the distal end of the first spacer mount portion to a recess distal end.

4. The method of claim 3, wherein the first aperture is defined on the first side and extends through the body of the first spacer mount portion and provides access to the recess, the second aperture is defined on the second side and extends through the body of the first spacer mount portion and provides access to the recess, the third aperture is defined on the recess distal end and extends through the body of the first spacer mount portion and provides access to the recess.

5. The method of claim 2, wherein said support member is also disposed within the third aperture of the first spacer mount portion.

6. The method of claim 2, wherein, the second attachment member first end is disposed through the first aperture of the first spacer mount portion, and the second attachment member second end is disposed through the second aperture of the first spacer mount portion.

7. The method of claim 2, wherein the first spacer body portion has a proximal end and a distal end; and wherein the body of the first spacer body portion defines a first side and a second side, each of the first side and the second side extending from the proximal end to the distal end of the first spacer body portion, the body of the first spacer body portion defining a first recess on the first side and a second recess on the second side.

8. The method of claim 7, wherein the first end of the second attachment member is disposed within the first recess defined by the first spacer body portion; and wherein the second end of the second attachment member is disposed within the second recess defined by the first spacer body portion.

9. The method of claim 1, wherein said first spacer body portion also defines an intermediate member disposed between the insert member and the articulating member.

10. The method of claim 9, wherein the aperture defined by the body of the first spacer body portion extends through the intermediate member.

11. The method of claim 1, wherein the body of the first spacer mount portion defines a first notch that extends into the body of the first spacer mount portion from the first side and toward the recess to a first notch base; and
    wherein the body of the first spacer mount portion defines a second notch that extends into the body of the first spacer mount portion from the second side and toward the recess to a second notch base.

12. The method of claim 11, wherein the first aperture defined by the first spacer mount portion is defined on the first notch base; and
    wherein the second aperture defined by the first spacer mount portion is defined on the second notch base.

13. The method of claim 1, wherein the recess defined by the first spacer mount portion has a first portion and a second portion, the first portion of the recess having a first length along the proximal end, the second portion of the recess having a second length along the proximal end, the first length greater than the second length.

14. The method of claim 13, wherein the first attachment member has a proximal end and a distal end; and
    wherein the body of the first attachment member defines an engagement member that has a first portion and a second portion, the first portion of the engagement member has a first length along the proximal end, the second portion of the engagement member has a second length along the proximal end, the first length of the first portion of the engagement member is substantially equal to the first length of the first portion of the recess of the first spacer mount portion, the second length of the second portion of the engagement member is substantially equal to the second length of the second portion of the recess of the first spacer mount portion.

15. The method of claim 14, wherein the body of the first attachment member defines a recess on the engagement member; and wherein the second attachment member is disposed within the recess defined on the engagement member.

16. The method of claim 1, wherein said subtalar spacer system further comprises a second spacer mount portion having a proximal end, distal end, and a body defining a recess and a bore, the recess extending into the body of the second spacer mount portion, the bore extending through the body of the second spacer mount portion;

a second spacer body portion having a body that defines an insert member, articulating member, and an aperture that extends through the body of the second spacer body portion, the insert member disposed within the recess of the second spacer mount portion, the articulating member of the second spacer body portion defining an articulating surface;

a third attachment member that is attached to the second spacer mount portion, the third attachment member having a body that defines a support member that extends through the aperture defined by the second spacer body portion;

a fourth attachment member that is attached to the second spacer mount portion; and a second fastener disposed through the bore of the second spacer mount portion and attaching the second spacer mount portion to a bone.

17. The method of claim 1, wherein said subtalar spacer system is implanted in the sinus tarsi of said foot.

18. The method of claim 1, wherein said method comprises attaching said first spacer mount portion to said bone and said bone is talus bone or calcaneous bone.

* * * * *